(12) United States Patent
Fujii

(10) Patent No.: US 6,485,483 B1
(45) Date of Patent: Nov. 26, 2002

(54) MEDICAL TUBE-CONNECTOR DEVICE

(75) Inventor: Junya Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 09/508,266

(22) PCT Filed: Jul. 9, 1999

(86) PCT No.: PCT/JP99/03757

§ 371 (c)(1),
(2), (4) Date: Mar. 8, 2000

(87) PCT Pub. No.: WO00/02617

PCT Pub. Date: Jan. 20, 2000

(30) Foreign Application Priority Data

Jul. 13, 1998 (JP) ............................................. 10-197737
Apr. 9, 1999 (JP) ............................................. 11-102003

(51) Int. Cl.[7] ............................................. A61M 25/16
(52) U.S. Cl. ...................................... 604/535; 604/537
(58) Field of Search ............................... 604/29, 30, 32, 604/33, 533–539, 905; 128/DIG. 12; 137/625.41, 625.46; 251/304

(56) References Cited

U.S. PATENT DOCUMENTS 3,048,192 A * 8/1962 Murphy ................. 137/625.42
3,078,848 A * 2/1963 Milbert ........................ 128/251
4,950,230 A 8/1990 Kendell
5,713,850 A 2/1998 Heilmann et al.

FOREIGN PATENT DOCUMENTS

| JP | 2-502882 | 9/1990 |
| JP | 5-31178 | 2/1993 |
| JP | 8-000725 | 1/1996 |
| JP | 8-155025 | 6/1996 |
| JP | 8-224300 | 9/1996 |

* cited by examiner

Primary Examiner—Michael J. Hayes
(74) Attorney, Agent, or Firm—Merchant & Gould, P.C.

(57) ABSTRACT

A medical tube-connector device that enables easy connection and disconnection without allowing channel ends to be touched by fingers. The first connector body includes a channel that can communicate with a tube, and is removably attached to the first connector body. The second connector body includes a channel and a concave part into which the protective cap can be inserted. A displaceable guide cap is attached to the second connector body. In a preparatory state, the concave part into which the protective cap can be inserted is open and the end of the channel is sealed. In the connected state, the end of the channel is open. The protective cap is maintained in the concave part so as to be detached from the first connector body and at the same time the channels of the first and second connector bodies communicate.

25 Claims, 26 Drawing Sheets

(a)

(b)

MEDICAL TUBE-CONNECTOR DEVICE

TECHNICAL FIELD

The present invention relates to a medical tube-connector device for connecting tubes forming a channel for a medical liquid, which is used for medical applications, particularly for peritoneal dialysis. Particularly, the present invention relates to a medical tube-connector device in which channel ends are not contaminated or damaged by fingers in connecting or disconnecting connectors and the connectors are connected and disconnected easily.

BACKGROUND ART

When peritoneal dialysis is operated, the inside of peritonea is filled with a dialysate having a concentration gradient with respect to a body fluid of a patient through a catheter introduced into the abdominal cavity passing through a abdominal wall of the patient. The peritonea of the patient function as a diaphragm, and toxin, a waste product, or the like inside the body of the patient is moved into the abdominal cavity. Then, the toxin, waste product, or the like inside the abdominal cavity is discharged to the outside of the body.

Concretely, extension tubes or the like that are connected to a dialysate bag, a drainage bag, and a catheter are connected to infuse a dialysate into the abdominal cavity and the dialysate is retained for a predetermined time (three to five hours). After that, a pooled liquid of toxin, waste products, or the like is discharged into the drainage bag. The dialysate is infused into the abdominal cavity of the patient through the tubes and the liquid of toxin, waste products, or the like also is discharged into the drainage bag through the tubes.

Thus, a twin bag system has been contrived, in which a dialysate bag and a drainage bag are connected with a Y-shaped connector or the like beforehand so that the patient can infuse the dialysate easily into the abdominal cavity or can discharge the pooled liquid easily.

However, while the dialysate is retained inside the abdominal cavity, it is more comfortable and preferable for a patient that the connected bags are disconnected from connectors for extension tubes compared to the case where the patient must carry such a dialysate bag and a drainage bag with him. In this case, when the connectors for the extension tubes are exposed to the air without having any protection, there is a fear that the connectors may be contaminated by bacteria or the like in the air. Therefore, it is desirable to cover the connectors with caps or the like. In the conventional twin bag system, caps mainly have been used for protecting the connectors from contamination.

However, in the case where liquids are replaced by a patient, the channel also is contaminated when the patient touches the connectors, the caps, or the like with his hands carelessly in attaching the caps to or detaching the caps from the connectors. As a result, the possibility that the inside of the abdominal cavity of the patient might be contaminated remains.

As a method for solving the above-mentioned problem, a structure having double walls formed at the connection ends of connectors to prevent fingers from touching the connector ends easily has been proposed as described in JP 5-31178 A. JP 8-000725 A discloses an automatic connection device for attaching and detaching a cap and connecting and disconnecting connectors automatically so that a patient can connect and disconnect the connectors without touching them directly with his hands.

However, even if such a double-wall structure as described in JP 5-31178 A was employed, it was not enough as a countermeasure against contamination. First, when connectors, or a connector and a cap are attached to or detached from each other, channel ends provided in the connectors are exposed to the outside air. Therefore, there was a possibility that the channel might be contaminated by floating fungus. Second, since the connectors are attached or detached by hands, it cannot be said that the open ends of the connectors are prevented perfectly from being touched by fingers. In other words, one of the connectors inevitably has a large external-wall diameter and therefore the possibility that the connectors might be touched by fingers still remains.

On the other hand, as described in JP8-000725 A, an apparatus of automating the attachment and detachment of a cap and the connection and disconnection of connectors is used in limited situations, since the apparatus has a complicated configuration and is expensive, and it is inconvenient for a patient to carry the apparatus with him all the time.

In the peritoneal dialysis, besides the contamination problem that might occur in attaching or detaching a cap or connectors as described above, there has been a problem of switching channels for infusing a fluid into and discharging a fluid from the abdominal cavity of a patient. That is to say, a switching device is required for switching channels easily without confusing the infusion of a dialysate and the discharge of a pooled fluid. Conventionally, the switching has been performed generally by a patient himself with his hands using a clamp. In view of the prevention of wrong operations, safety, or the like, however, various devices for controlling the switching have been contrived. For instance, JP 8-224300 A discloses a rotary controller as a device for controlling the flow of fluids. Further, JP 2-502882 A discloses a flow controller using a special three-way valve.

However, in the conventional method in which a patient controls the flow by himself using a clamp, there has been a possibility that switching failure causes the back flow of a fluid into his body or wasteful discharge of a dialysate into a drainage bag.

In addition, in a conventional channel-switching device, channels can be switched, but a patient is required to attach or detach a connector of a tube and a connector of a dialysate bag, or a connector and a cap to or from each other by himself with his hands. In this case, therefore, the possibility that the connectors or the cap might be contaminated by careless operations or mistakes by a patient himself still remains. Furthermore, since the cap also is replaced by a patient himself with his hands, there also has been a possibility that an unused cap might be contaminated at the time of the replacement.

DISCLOSURE OF THE INVENTION

The present invention aims to solve the aforementioned disadvantages in conventional techniques and to provide a medical tube-connector device having a configuration in which in order to prevent the contamination by fingers or wrong operations, which might occur in disconnecting or connecting connectors, caps are detached from or attached to the connectors without exposing channel ends provided in the connectors when the connectors are connected to or disconnected from each other.

Further, the present invention aims to provide a medical tube-connector device that enables the connection or disconnection of connectors accompanied with the detachment or attachment of caps to be operated easily without using special devices or tools, while keeping the channels of the connectors from being contaminated.

In addition, the present invention aims to provide a medical tube-connector device that can facilitate channel switching, can prevent possible contamination or wrong operations in connecting or disconnecting connectors, and enables a patient to replace caps in connecting and disconnecting the connectors without touching connection parts directly with his hands.

In order to solve the above-mentioned problems, a medical tube-connector device of the present invention includes two connectors for connecting tubes and the two connectors can be connected to or disconnected from each other. The medical tube-connector device is provided with a first connector including a first connector body and a protective cap and a second connector including a second connector body and a guide cap. The first connector body has a channel extending through its inside and can be connected to a tube at one end of the channel. The protective cap can be attached to or detached from the first connector body for covering and sealing the other end of the channel in the state in which the protective cap has been attached to the first connector body. The second connector body has a channel extending through its inside and a concave part into which the protective cap of the first connector can be inserted. The second connector body can be connected to a tube at one end of the channel. The guide cap can be displaced with respect to the second connector body and is provided with a cover portion formed for covering and sealing the other end of the channel in the second connector body. The second connector body and the guide cap can be brought into a preparatory state or a connected state by their relative displacement. In the preparatory state, the concave part of the second connector body is open and the other end of the channel is sealed by the cover portion. In the connected state, the other end of the channel is open. By inserting the first connector with the protective cap attached into the concave part in the preparatory state and then bringing the second connector body and the guide cap into the connected state, the protective cap is moved while being retained in the concave part so as to be detached from the first connector body and at the same time the first connector body and the second connector body are connected, thus allowing their channels to communicate.

According to the aforementioned configuration, the detachment and attachment of the protective cap and the sealing and opening of the channel end of the second connector body can be carried out inside the connector device upon the operations for connecting and disconnecting the connectors. Therefore, the channels are not exposed to the outside air. Consequently, the channel ends of the connectors can be prevented from being contaminated by outside floating bacteria. Further, since the connectors are not connected and disconnected by hands, the fear that fingers might touch the channel ends can be solved. In addition, the connecting and disconnecting operations can be carried out merely by inserting the first connector into the second connector and rotating the second connector body without using special tools, which is very easy.

In the above-mentioned configuration, the second connector may have the following configuration. The second connector may include a casing having an annular shape and functioning as a guide cap and a rotor that is formed of a substantially cylindrical body mounted rotatably inside the casing and that functions as the second connector body. The casing includes, at its periphery: at least one inflow/outflow port for liquids, which can be connected to a tube; and an insertion opening into which the first connector can be inserted. The rotor includes: a fluid channel extending through the inside of the cylindrical body and forming inflow/outflow ports on the peripheral surface of the cylindrical body; and at least one cap receiving recess that is formed on the peripheral surface of the cylindrical body and that can receive a protective cap attached to the first connector. The rotor and the casing can be brought into a preparatory state or a connected state depending on their relative rotational positions. In the preparatory state, the insertion opening of the casing opposes the cap receiving recess in the rotor and thus the inflow/outflow ports of the rotor are sealed by the casing. In the connected state, the insertion opening of the casing opposes one of the inflow/outflow ports of the rotor, and an inflow/outflow port of the casing and the other inflow/outflow port of the rotor communicate with each other.

The medical tube-connector device with this configuration can be formed so that in the connected state, the first connector body is maintained by being fitted at a periphery of the rotor. This enables the first connector body to be maintained by the rotor reliably, thus preventing the tube from being detached or the like during a dialysis operation.

It is preferable that the protective cap can be detached from or attached to the first connector body by its sliding movement in the direction substantially orthogonal to the direction of the channel. This enables the operation for detaching and attaching the protective cap by the rotation of the rotor to be carried out easily.

It is preferable that the protective cap is attached to the first connector body through the fitting between a convex part with a T-shaped cross section provided in the protective cap and a concave part with a T-shaped cross section provided in the first connector body, and a convex part with the same T-shaped cross section as in the protective cap is provided at the periphery of the rotor except for the insertion opening. In this case, the protective cap can slide in the sideways direction easily and the protective cap and the first connector body are not detached easily in the channel direction. As the cross sectional shape of the cap, any cross sectional shapes can be used as long as the shapes have the same characteristics. For instance, the cross section of the cap may have a trapezoidal shape, a round shape, or an inverse triangular shape.

The second connector establishes an invention by itself, which is one of two connectors constituting a medical tube-connector device according to the present invention. A connector according to the present invention includes a casing and a rotor. The casing has an annular shape and includes, at its periphery, at least one inflow/outflow port for liquids, which can be connected to a tube, and an insertion opening into which the other connector can be inserted together with a protective cap for sealing an opening of the other connector. The rotor is formed of a substantially cylindrical body mounted rotatably inside the casing. The rotor includes: a fluid channel extending through the inside of the cylindrical body and forming inflow/outflow ports on the peripheral surface of the cylindrical body; and at least one cap receiving recess that is formed on the peripheral surface of the cylindrical body and that can receive the protective cap for sealing the opening of the other connector. The rotor and the casing can be brought into a preparatory state or a connected state depending on their relative rotational positions. In the preparatory state, the insertion opening of the casing opposes the cap receiving recess in the rotor and thus the inflow/outflow ports in the rotor are sealed by the casing. In the connected state, the insertion opening of the casing opposes one of the inflow/outflow ports of the rotor, and the inflow/outflow port of the casing and the other inflow/outflow port of the rotor communicate with each other.

Preferably, this connector is formed so that the rotor includes at least two cap receiving recesses and the insertion opening of the casing can oppose any of the cap receiving recesses by the relative rotational movement between the rotor and the casing. According to this, a configuration for replacing the protective cap automatically by rotation can be obtained. In this case, any configuration may be employed as long as an unused cap can be supplied. Therefore, the connector may have a configuration in which an unused cap may have been supplied from the beginning or an unused cap can be replenished later.

Further, the following configuration also may be employed. Unused protective caps are supplied to the cap receiving recesses while at least one cap receiving recess is kept empty and the rotor is rotated from the state in which the rotor is connected with the other connector, to have the positional relationship in which the insertion opening of the casing opposes any one of the cap receiving recesses in which the unused protective caps have been supplied, thus attaching an unused protective cap to the other connector. In this case, a patient can replace caps without touching connection parts directly with his hands in detaching and attaching the caps, thus eliminating the possibility that the patient touches the connectors, the caps, or the like carelessly with his hands to cause the contamination of the channel.

The following configuration also can be employed. The casing has at least two of the inflow/outflow ports for liquids, one of the inflow/outflow ports communicates selectively with one of the inflow/outflow ports of the rotor by the rotational movement of the rotor, and at the same time, the other inflow/outflow port of the rotor opposes the insertion opening of the casing. According to this configuration, a connector in which channels can be switched easily can be obtained.

In this configuration, it is preferable that the casing has two of the inflow/outflow ports for liquids, and the inflow/outflow ports and the insertion opening are spaced substantially at 120 degrees at the periphery of the casing. This enables channels to be switched easily in three directions without having a complicated mechanism such as a three-way valve.

The first connector as one of connectors constituting a medical tube-connector device according to the present invention establishes an invention by itself. That is, a connector according to the present invention includes: a connector body that is attached to an end of a tube and has a through hole that communicates with the tube and a protective cap that is attached to the connector body and seals an opening of the connector body. The connector has a configuration in which the protective cap is detached from or attached to the connector body by being slid in the direction substantially orthogonal to the axial direction of the through hole. This configuration can prevent the channel end from being contaminated and can facilitate the connection operation.

It is preferred to employ the configuration in which the protective cap has a convex part with a T-shaped cross section, the connector body has a concave part with a T-shaped cross section, and the protective cap and the connector body are coupled by the fitting between the convex part and the concave part. According to this configuration, the protective cap can slide in the sideways direction easily and a form in which the protective cap and the connector body are not separated easily in the direction of the channel can be achieved. In this case, any shapes can be used as the cross sectional shape of the cap as long as the shapes have the same characteristics. For instance, a trapezoidal shape, a round shape, or an inverse triangular shape can be applied.

The medical tube-connector device with the configuration described first can be formed so that the protective cap is attached to the first connector body and at the same time the channel end of the second connector body is sealed by the cover portion by relatively displacing the second connector body and the guide cap from the connected state and thus restoring them into the preparatory state.

Preferably, the medical tube-connector device with the configuration described first is formed so that in the connected state, the guide cap can be detached from the second connector body in a state where the first connector body and the second connector body are maintained in a coupled state.

In this configuration, preferably a receiving part capable of receiving the protective cap is formed in the guide cap adjacent to the place where the first connector is inserted, and in the connected state, the protective cap that has been moved while having been maintained in the concave part is received and maintained in the receiving part. This configuration is useful particularly when the guide cap is detached from the second connector body in employing the route in which the preparatory state is restored directly from the connected state (i.e. the preparatory state→the connected state→the preparatory state). When it is not necessary to detach the guide cap after both the connectors have been connected, a means for maintaining the protective cap is not particularly necessary to be provided.

The first connector and the second connector can be formed so as to maintain the connected state against a pulling force in the direction of the channel and so as to be disconnectable by their sliding movements with respect to each other in the direction orthogonal to the direction of the channel.

Preferably, the medical tube-connector device with the configuration described first is constructed so that: the protective cap can be attached to or detached from the first connector body by its sliding movement along a circular arc; the second connector body and the guide cap can be displaced relatively by their sliding movements along a circular arc; the circular arc corresponding to the sliding face for the sliding movement between the first connector body and the protective cap has the same radius as that of the circular arc corresponding to the sliding face for the sliding movements between the second connector body and the guide cap; and the sliding face between the first connector body and the protective cap and the sliding face between the second connector body and the guide cap are arranged on the same circular arc when the first connector is inserted into the concave part from the protective cap side in the preparatory state. Further preferably, the medical tube-connector device is formed so that the center of the circular arc corresponding to the sliding face between the second connector body and the guide cap is positioned inside the second connector body. According to these configurations, since the attachment and detachment are carried out by the rotation, a force can be applied easily, thus facilitating the operation.

Moreover, in the above-mentioned configuration, it is preferable that: the first connector body has any one of a concave engagement part and a convex engagement part, each of which has a T-shaped cross section orthogonal to a direction of its sliding movement; the protective cap has the other one of the concave engagement part and the convex engagement part; the concave engagement part and the convex engagement part are fitted to each other to lead the sliding movements of the first connector body and the protective cap; and by the fitting, the protective cap is maintained in the first connector body. This configuration ensures the engagement of the protective cap with the first connector body and also facilitates the detachment and attachment of the protective cap.

Further, preferably, the second connector body has the convex engagement part with the T-shaped cross section when the first connector body has the concave engagement part with the T-shaped cross section, and the second connector body has the concave engagement part with the T-shaped cross section when the first connector body has the convex engagement, the convex and concave engagement parts of the protective cap and the second connector body being arranged on the same circular arc when the protective cap is inserted into the concave engagement part in the preparatory state, and the convex and concave engagement parts of the first connector body and the second connector body are fitted in the connected state, thus coupling the first connector body and the second connector body. According to this configuration, in connecting the connectors, the second connector body is fitted to the first connector body instead of the detached protective cap, and therefore the engagement structure of the both is very simple.

Furthermore, it is preferable that the guide gap has a wall for covering the protective cap in the connected state. According to this configuration, the protective cap can be protected excellently when the connectors are connected.

Preferably, the guide cap has a handle extending along the inserted first connector body. When the second connector body is rotated with the first connector body being held together with the handle, the connection between the first connector body and the second connector body can be operated stably and easily.

Next, another type of invention of the second connector constituting the medical tube-connector device according to the present invention will be described. A connector according to the present invention includes a connector body and a guide cap. The connector body includes a channel extending through its inside and a concave part into which a protective cap for sealing an opening of the other connector can be inserted. The connector body can be connected to a tube at one end of the channel. The guide cap can be displaced with respect to the connector body and is provided with a cover portion for covering and sealing the other end of the channel of the connector body. The connector body and the guide cap can be brought into a preparatory state or a connected state by their relative displacement. In the preparatory state, the concave part of the connector body is open and the other end of the channel is sealed by the cover portion. In the connected state, the other end of the channel is open.

In addition, a cap for replacement according to the present invention is formed by the combination of the guide cap and the protective cap that are included in a medical tube-connector device according to the present invention. The cap for replacement of the present invention includes: the guide cap provided with a cover portion that can cover and seal the other end of the channel of the second connector body, an opening adjacent to the cover portion, and a receiving part that is adjacent to the opening and that can receive the protective cap; and the protective cap received in the receiving part of the guide cap.

BRIEF DESCRIPTION OF DRAWINGS

FIG. 6(a) is its plan view and FIG. 6(b) is its cross sectional view;

FIG. 18(a) is its perspective view, FIG. 18(b) its front view, and FIG. 18(c) a cross sectional view taken along line A—A in FIG. 18(b);

FIG. 21(a) is its plan view, FIG. 21(b) its front view, and FIG. 21(c) its rear view;

FIG. 22(a) is its plan view and FIG. 22(b) a cross sectional view taken along line A—A in FIG. 22(a);

FIG. 24 shows the state shown in FIG. 23 (c) with a guide cap being detached and FIG. 24(a) is its plan view and FIG. 24(b) its front view;

BEST MODE FOR CARRYING OUT THE INVENTION

First Embodiment

A medical tube-connector device according to a first embodiment of the present invention is described with reference to FIG. 1 to FIG. 15 as follows.

Figure 1:
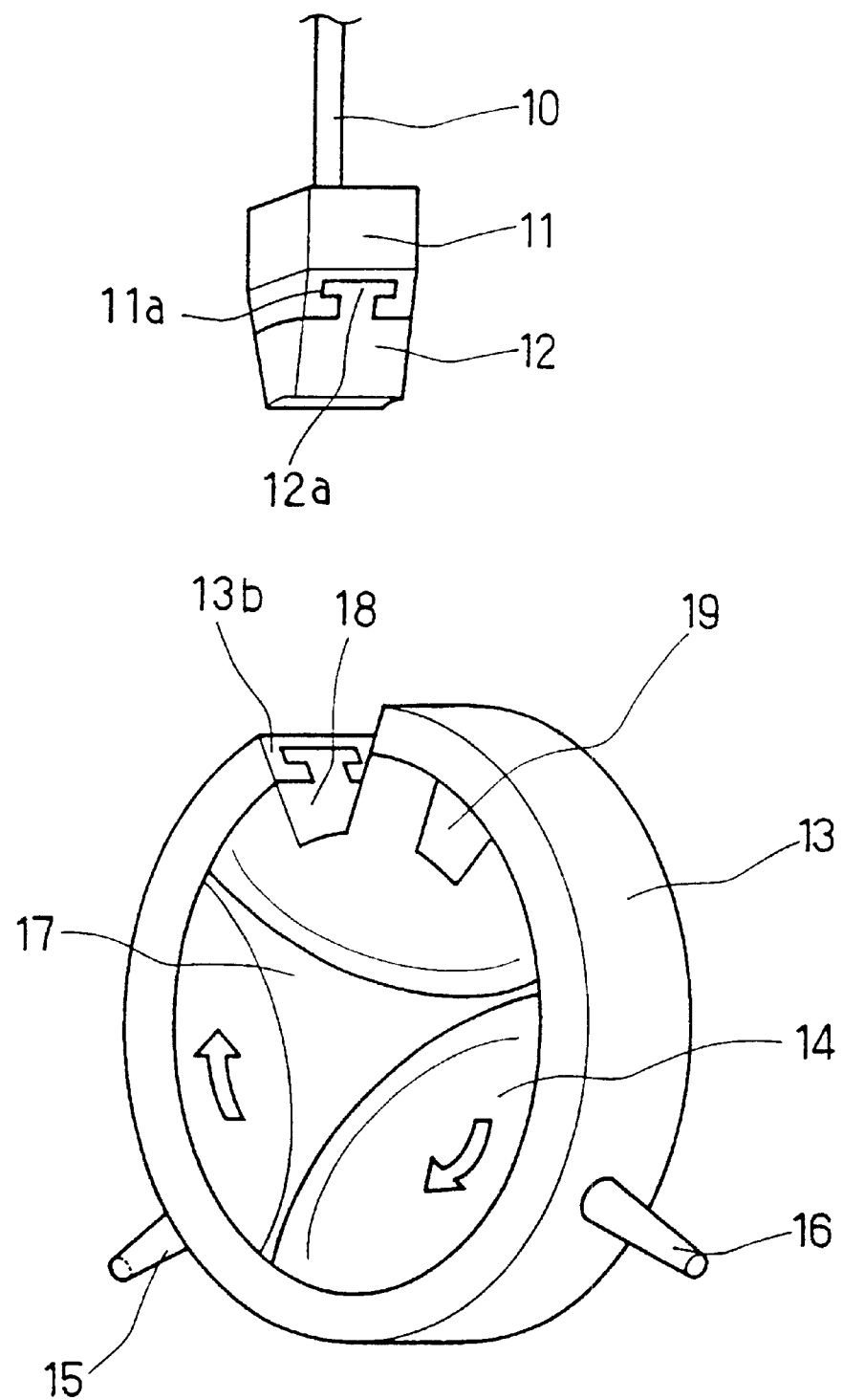
FIG. 1 is a perspective view of a medical tube-connector device according to a first embodiment of the present invention.

FIG. 1 is a perspective view of a medical tube-connector device according to an embodiment of the present invention. In FIG. 1, numeral indicates a tube from a catheter, numeral 11 a first connector body, and numeral 12 a protective cap attached to an end of the first connector body 11. The first connector body 11 and the protective cap 12 form a first connector. The first connector body 11 and the protective cap 12 are fitted to each other with a convex part 12a with a T-shaped cross section formed in the protective cap 12 being inserted into a concave part 11a with a T-shaped cross section formed in the first connector body 11.

Numeral 13 denotes a casing and numeral 14 a cylindrical rotor positioned inside the casing 13. They form a second connector. Materials of the casing 13 and the rotor 14 are required to be light and not to be damaged easily, since they are handled by a patient. Examples of such materials include polypropylene, polycarbonate, or the like. As the size of the casing as a whole, an approximate palm-size is preferred, so that the patient can handle it easily by himself.

The casing 13 has a dialysate infusion port 15 and a drainage discharge port 16. The dialysate infusion port 15 and the drainage discharge port 16 are connected to a dialysate bag and a drainage bag, respectively. Further, the casing 13 has an insertion opening 13b and forms a guide cap. The rotor 14 forms a second connector body and has a grip 17 on its side face, which is used for being rotated, and a cap receiving part 18 in a circumferential portion of its cylindrical body. The cap receiving part 18 receives the protective cap 12 attached to the first connector body 11. FIG. 1 shows the state in which the position of the insertion opening 13b corresponds to the position of the cap receiving part 18. Numeral 19 indicates a cap receiving part for receiving an unused protective cap for replacement. When the casing 13 and the rotor 14 are rotated with respect to each other to bring the insertion opening 13b and the cap receiving part 18 into the state in which their positions correspond to each other as shown in the figure, the first connector can be inserted to allow the protective cap 12 to be received in the cap receiving part 18.

Figure 2:
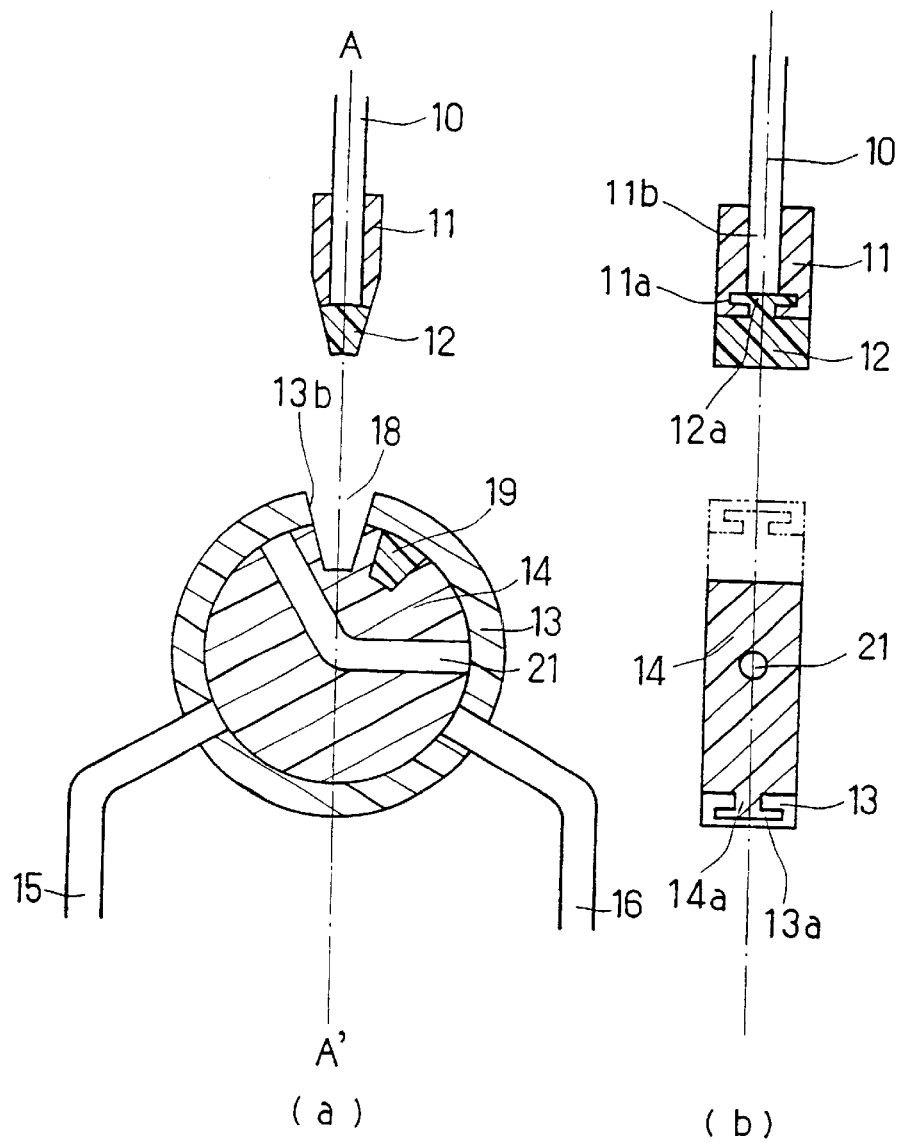
FIG. 2 is a cross sectional view of the medical tube-connection device shown in FIG. 1.

FIG. 2 shows cross sectional views of the medical tube-connector device shown in FIG. 1. FIG. 2(a) is a cross sectional plan view and FIG. 2(b) shows the cross section taken along line A–A' in FIG. 2(a). The first connector body 11 has a through hole 11b serving as a channel communicating with a tube 10. In the rotor 14, a channel 21 through which liquids such as a dialysate or the like flow is formed. In the channel 21, an inflow port and an outflow port form an angle of 120 degrees with each other. The insertion opening 13b of the casing 13, the dialysate infusion port 15, and the drainage discharge port 16 are arranged at angles of 120 degrees with one another. Therefore, by rotating the rotor 14, the channel 21 can be varied to three modes of channels including one from the tube 10 to the drainage discharge port 16, one from the dialysate infusion port 15 to the drainage discharge port 16, and one from the dialysate infusion port 15 to the tube 10. The shape of the channel is not limited to the bent form as in the present embodiment. A shape forming a circular arc or a linear shape also can be used.

The shape of the protective cap 12 positioned at the end of the tube is not particularly limited and may be a rectangular shape, a cylindrical shape, or the like. However, it is preferable that the protective cap 12 has a wedge shape, since the wedge shape facilitates the detachment and attachment of the protective cap 12 with respect to the second connector, the detachment of the protective cap 12 by the rotation of the rotor 14, and also the movement of the protective cap 12 by the rotation. Furthermore, the above-mentioned shape also serves effectively for preventing liquid leakage when the fluid channel is linked in a connected state.

As shown in the cross sectional view taken along line A–A', the protective cap 12 and the first connector body 11 are fitted to each other through a concave part 11a and a convex part 12a, each of which has a T-shaped cross section. The first connector body 11 and the protective cap 12 slide to be separated from each other by the rotation of the rotor 14 and the first connector body 11 is fitted to a rib 14a forming a convex part with a T-shaped cross section that is formed at the periphery of the rotor 14. An engagement groove 13a is formed at the inner periphery of the casing 13 all around and the rib 14a is formed at the outer periphery of the rotor 14 so as to engage with the groove.

In the above-mentioned configuration, for preventing wrong operations by a patient, it is preferable that when the channel 21 is rotated and fitted to the position of the dialysate infusion port 15, the drainage discharge port 16, or the cap receiving part 18, the channel 21 is fixed with click-stopped feeling. Alternatively, the fitting position may be displayed at a designated place. Further, it also is effective for preventing wrong operations to employ the configuration in which the rotor 14 can rotate only in one direction. The casing 13 and the rotor 14 may be formed to be transparent or translucent so that actual liquid flow can be checked visually.

Figure 3:
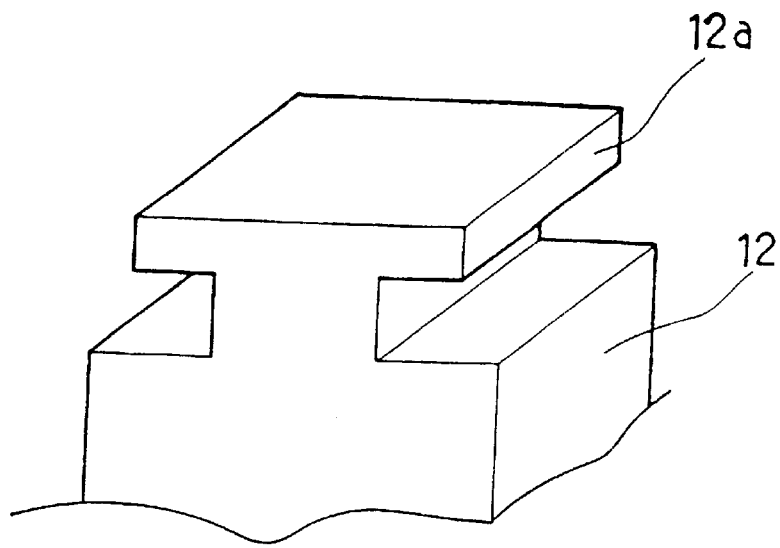
FIG. 3 is an enlarged perspective view of the coupling part of a protective cap.

FIG. 3 is an enlarged view of the engagement part of the protective cap 12. The protective cap 12 has the convex part 12a with a T-shaped cross section. As described above, the same convex part with a T-shaped cross section as in the protective cap 12 also is formed at the periphery of the rotor 14. On the other hand, the first connector body 11 has the concave part with a T-shaped cross section into which the convex part is fitted as described above.

Figure 4:
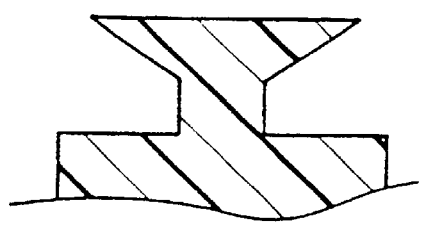
FIG. 4 is an enlarged cross sectional view showing another example of the coupling part of the protective cap.
Figure 5:
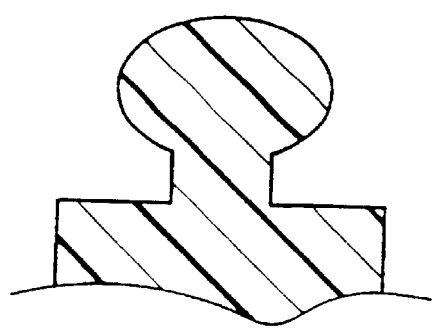
FIG. 5 is an enlarged cross sectional view showing further example of the coupling part of the protective cap.

The cross sectional form of the part to be coupled with the first connector body in the protective cap is not limited to the T-shaped type as shown in FIG. 3. For instance, it may have a trapezoidal shape as shown in FIG. 4 or a circular or elliptical shape as shown in FIG. 5. Any cross sectional forms are acceptable as long as the protective cap is not detached easily in the longitudinal direction when being fitted.

Figure 6:
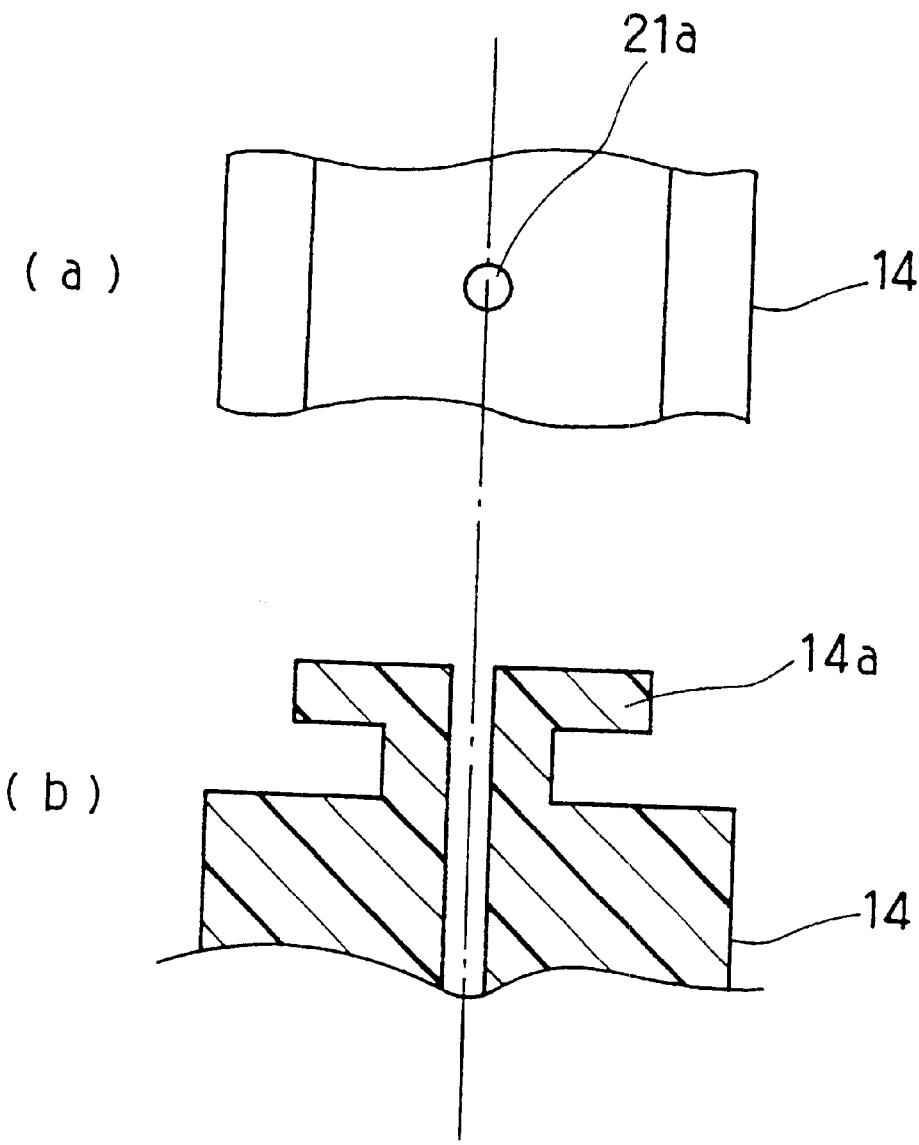
FIG. 6 shows a part of a rotor.

No matter what form the cross section of the part to be coupled has, a convex part having the same cross sectional shape is formed at the periphery of the rotor 14 and a hole is formed to serve as an inflow/outflow port of the channel 21 shown in FIG. 2 at the center of the convex part formed. In the case of the T-shaped cross section, the inflow/outflow port 21a is formed as shown in FIG. 6.

Figure 7:
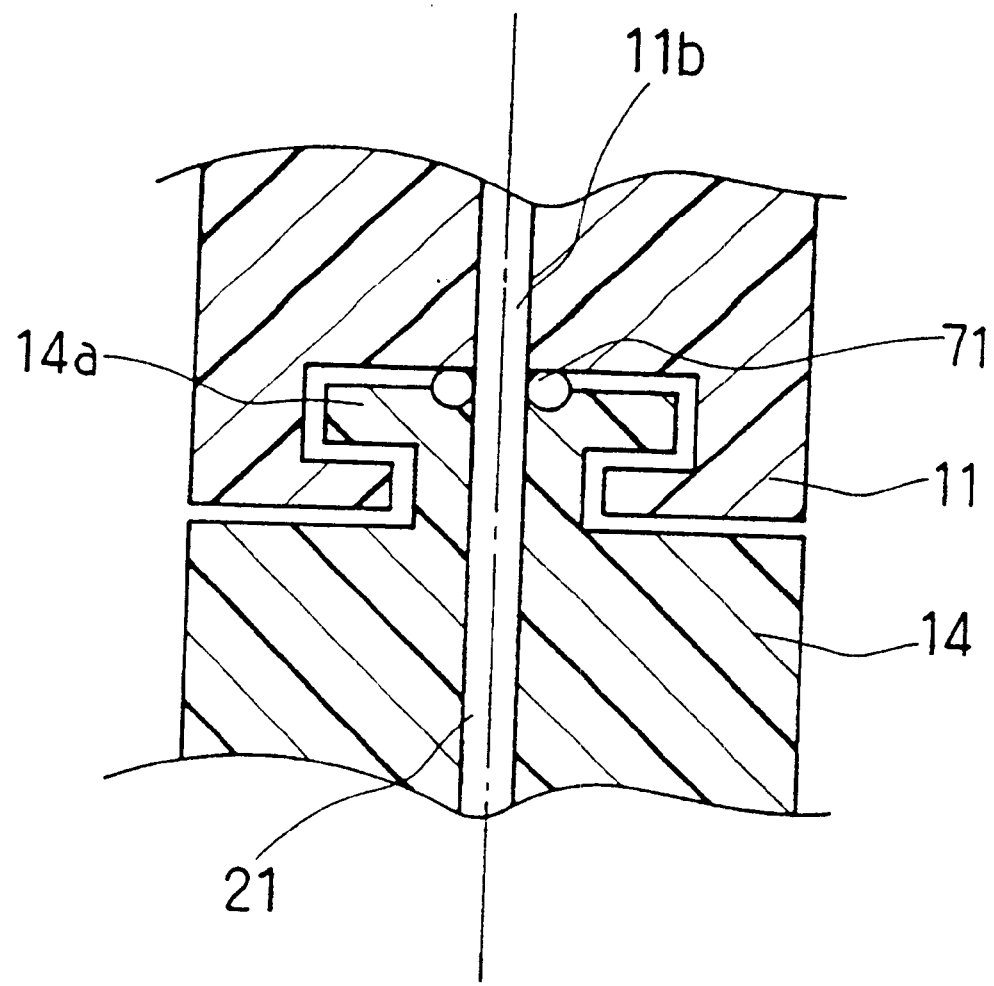
FIG. 7 is a cross sectional view showing a coupling structure of a protective cap in the medical tube-connector device shown in FIG. 1.

FIG. 7 is a cross sectional view showing a part of the medical tube-connector device shown in FIG. 1 and shows the connected state between the first connector body 11 and the rotor 14. When the rotor 14 rotates and the channel 21 is linked to the through hole 11b of the first connector body 11, a dialysate or drainage can flow inside the rotor 14. In this case, it is necessary to take some measures to prevent the liquid from leaking to the outside. Therefore, by attaching an "O"-ring 71 or the like to the convex part 14a formed at the periphery of the rotor 14, the leakage of the dialysate or drainage can be prevented in the connected state. It is preferable that the "O"-ring or the like is manufactured using an elastomeric material such as silicone rubber or the like.

The operation of the medical tube-connector device shown in FIG. 1 is described with reference to FIGS. 8 to 13 as follows.

Figure 8:
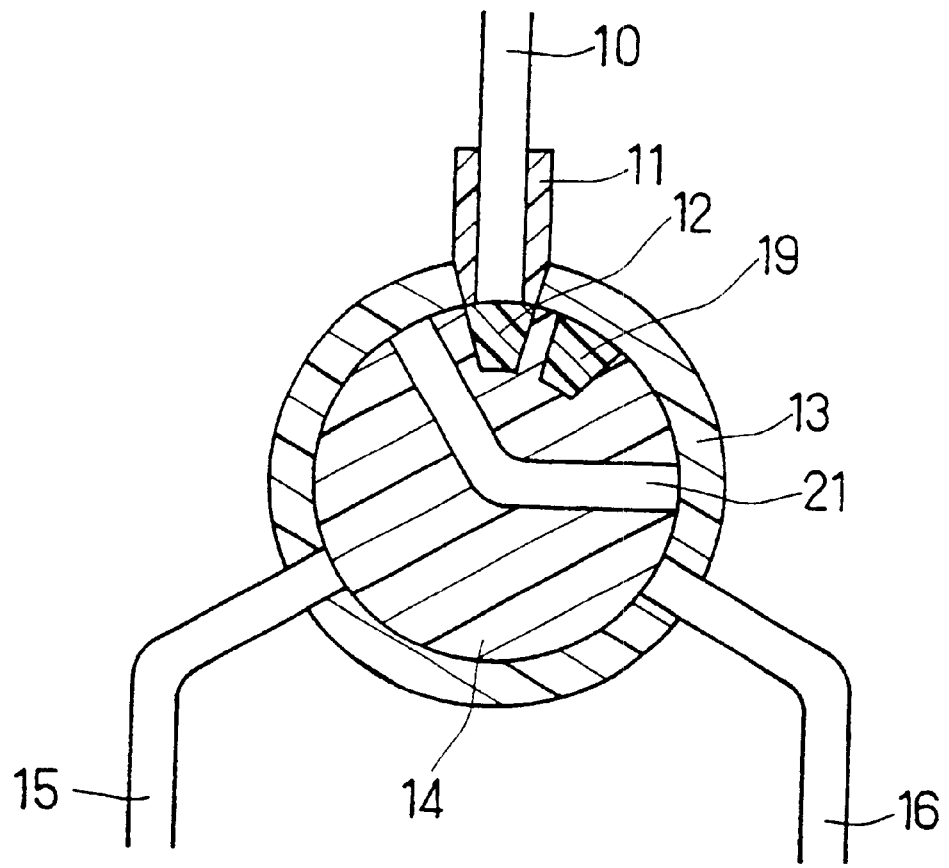
FIGS. 8 to 13 are cross sectional views for explaining the operation of the medical tube-connector device shown in FIG. 1.

As shown in FIG. 8, the first connector body 11 is inserted together with the protective cap 12 from the insertion opening 13b.

Figure 9:
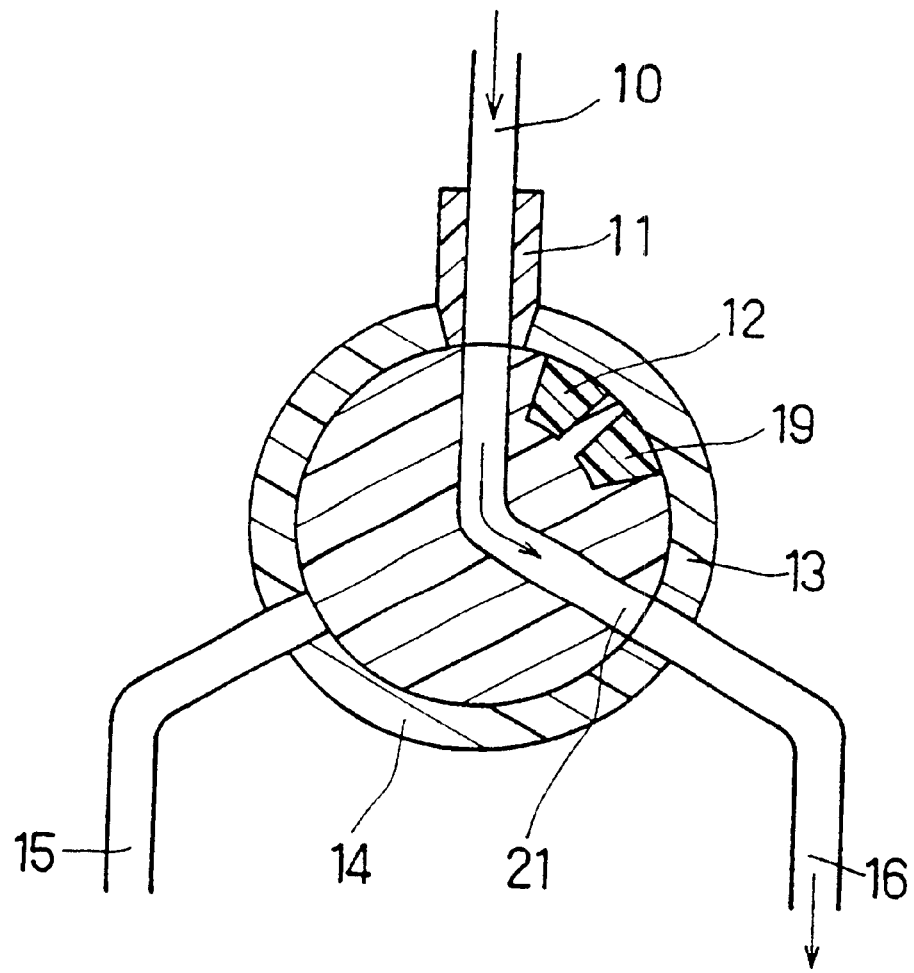

Then, the rotor 14 is rotated with the first connector being maintained as shown in FIG. 9 to link the tube 10 and the drainage discharge port 16 through the channel 21. By the rotation, the convex part formed at the periphery of the rotor 14 and the concave part of the first connector body 11 are fitted to each other. Thus, the first connector body 11 is maintained by the rotor 14. In this manner, the tube 10 is linked to the drainage bag, which enables the liquid pooled inside peritonea to be discharged to the drainage bag.

Figure 10:
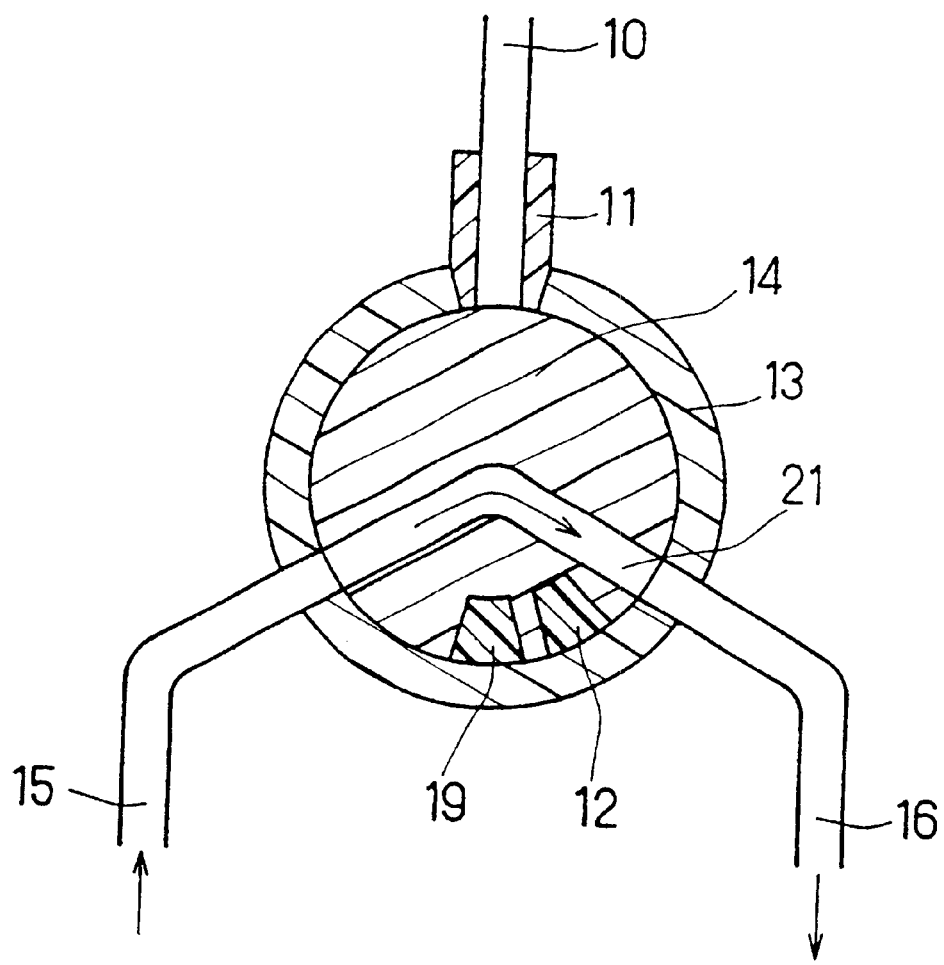
Figure 11:
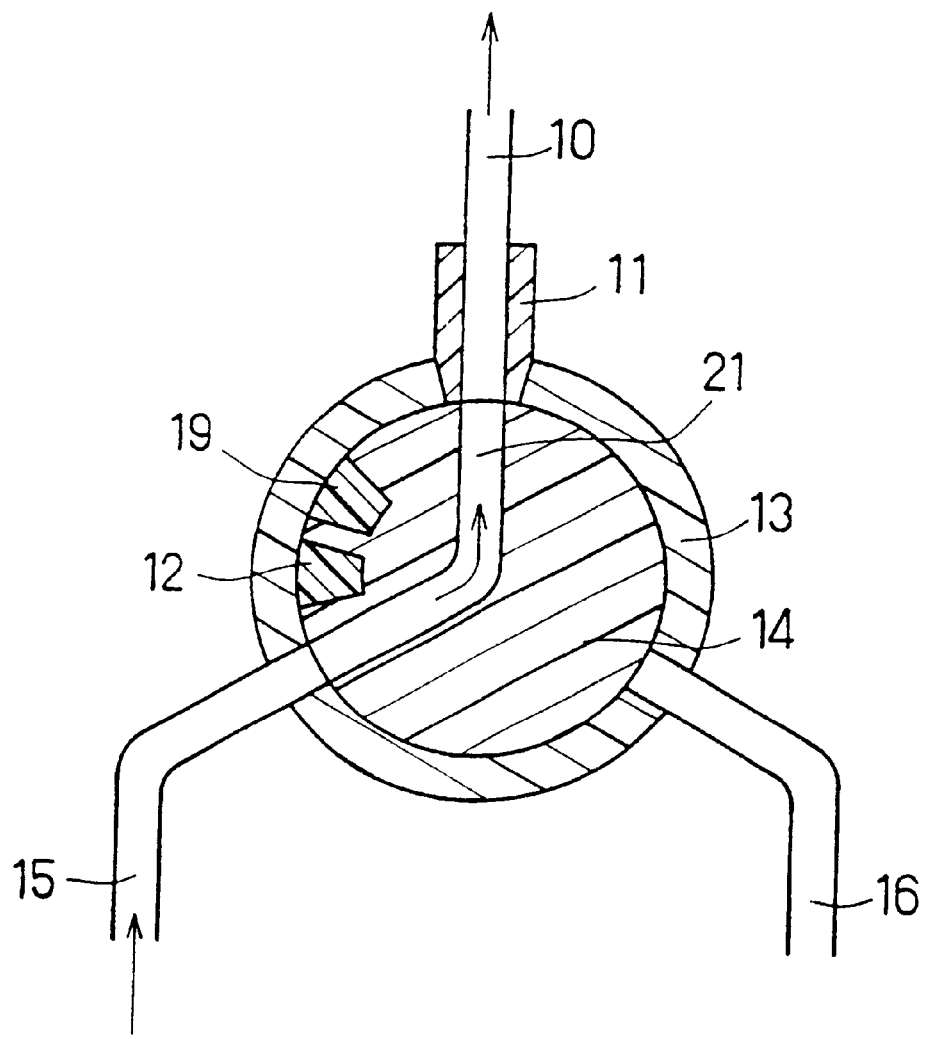

Next, the rotor 14 is rotated 120 degrees as shown in FIG. 10 to link the drainage discharge port 16 and the dialysate infusion port 15 through the channel 21. By discharging the dialysate directly to the drainage bag, the rest of the drainage adhering to the inside of the channel 21 inside the rotor 14 is washed, which provides a priming operation in which the inside of the channel 21 is filled with fluid. Such an operation is carried out for washing and priming of the channel. After the washing (priming) operation is completed, the rotor 14 is further rotated 120 degrees as shown in FIG. 11 to link the dialysate infusion port 15 and the tube 10 through the channel 21. Thus, the dialysate is infused into a body.

Figure 12:
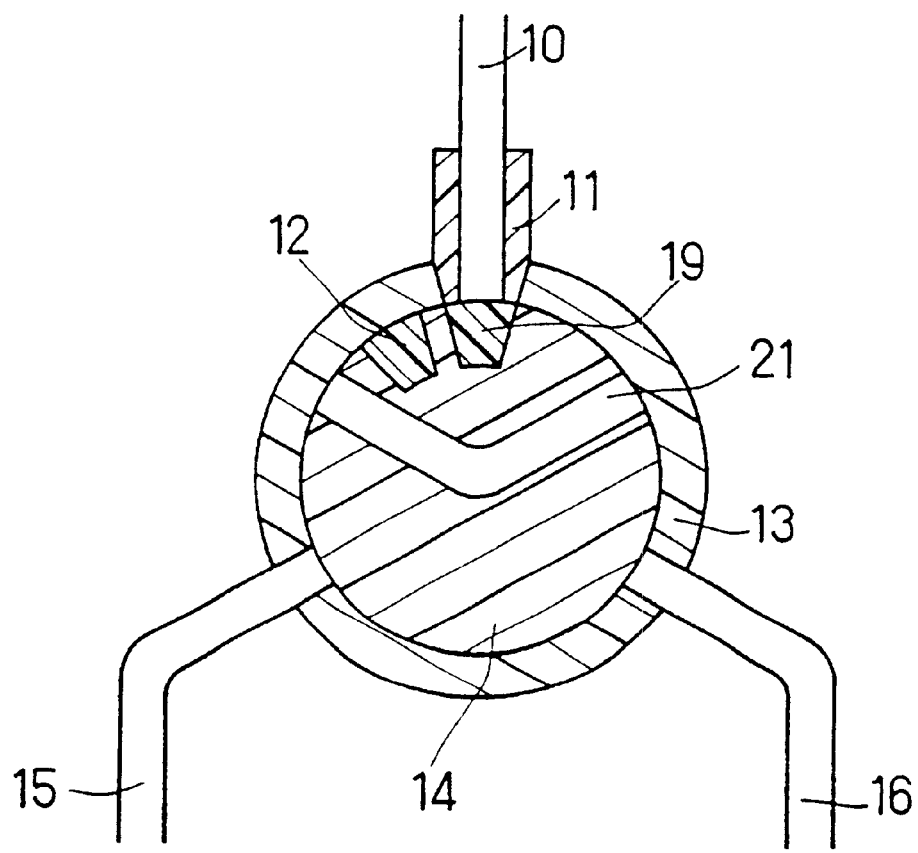
Figure 13:
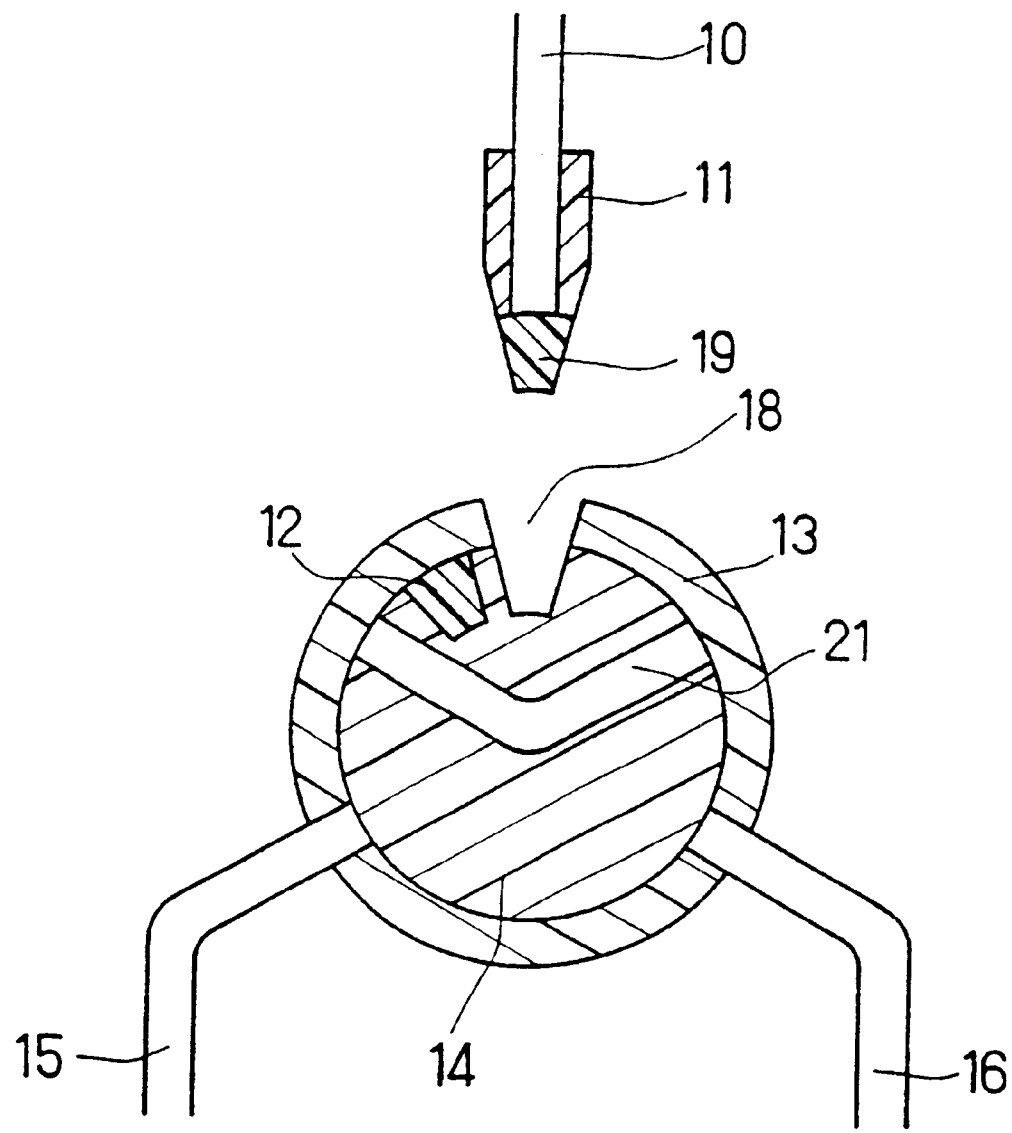

Upon the completion of the operation for infusing the dialysate, an unused protective cap 19 is fitted to the first connector body 11 by rotating the rotor 14 to be in the state shown in FIG. 12. The unused protective cap 19 is unlocked by being fitted to the first connector body 11 and is detached from the rotor 14. Thus, the tube 10 can be separated from the second connector. In other words, as shown in FIG. 13, since the tube 10 is disconnected from the device with the unused protective cap 19 being attached to the first connector body 11, the detachment, attachment, or replacement of the protective cap can be completed while the channel is not contaminated by the hands of a patient. Thus, the dialysis operation can be carried out easily with cleanliness being secured.

In order to maintain the coupling between the protective cap 12 and the rotor 14 when the first connector body 11 is inserted as shown in FIG. 8, a mechanism utilizing a spring-like elastic body or a mechanical locking system can be used.

Figure 14:
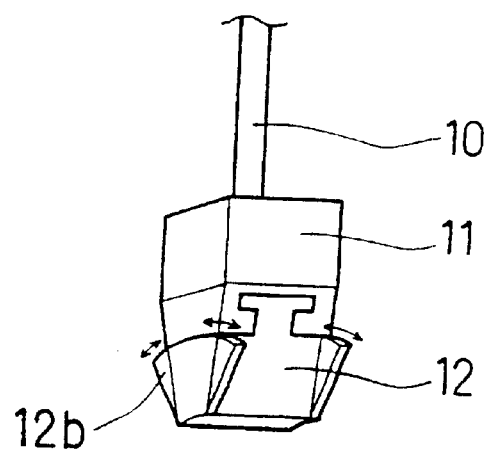
FIG. 14 is a perspective view showing a modified example of the medical tube-connector device according to the first embodiment of the present invention.
Figure 14:
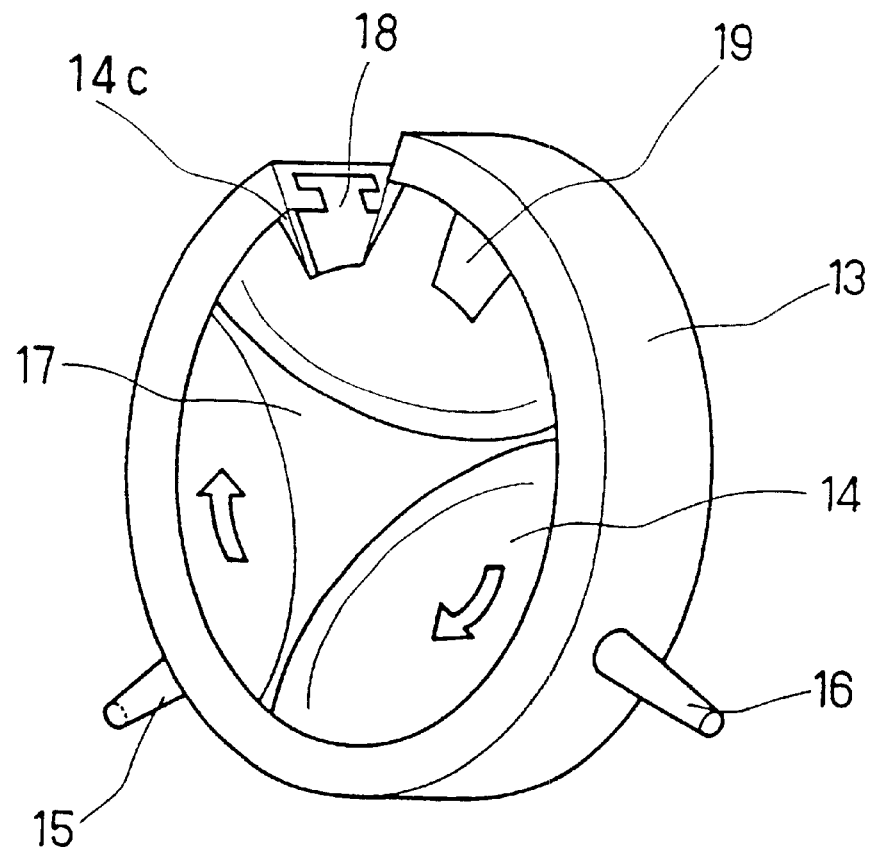

For instance, as shown in FIG. 14, retaining parts 12b that can stick out and retract by the elasticity of its material itself or by a mechanism such as a spring or the like are provided in the protective cap 12, and recesses 14c that can be engaged with the retaining parts 12b are provided in the rotor 14. Thus, when inserted into the cap receiving recess 18 together with the protective cap 12, the first connector is locked by the retaining parts 12b, so that the first connector cannot be disconnected easily even in the state in which the rotor 14 has not been rotated.

Figure 15:
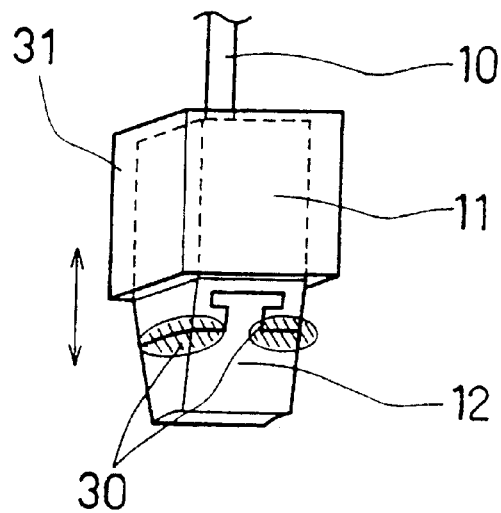
FIG. 15 is a perspective view showing another modified example of the medical tube-connector device according to the first embodiment of the present invention.
Figure 15:
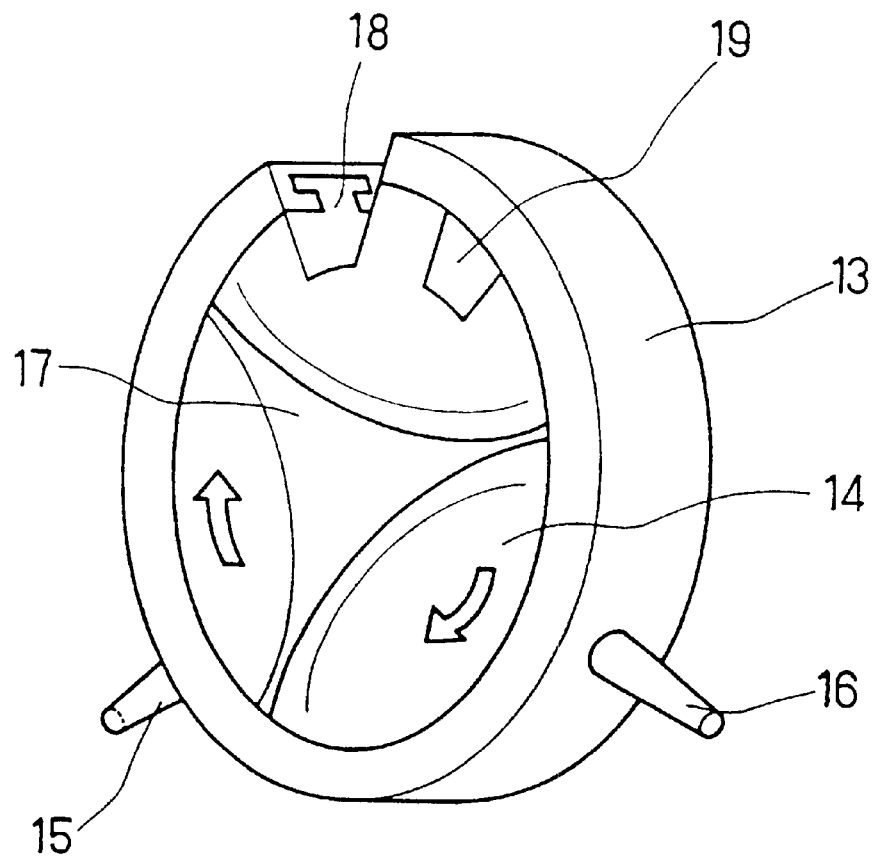

Furthermore, as shown in FIG. 15, it is not preferable in the use of the device that the vicinity 30 of the portion where the first connector body 11 and the protective cap 12 are fitted is contaminated by bacteria in the air or the like. Therefore, it is effective to provide a protective cover 31 outside the first connector body 11, which can be moved in the channel direction. In other words, when the first connector body 11 is not used, the vicinity 30 of the coupled portion is protected by moving down the protective cover 31 so that the protective cap 12 is covered, and when the first connector body 11 is used, the protective cover 31 is moved up.

Figure 16:
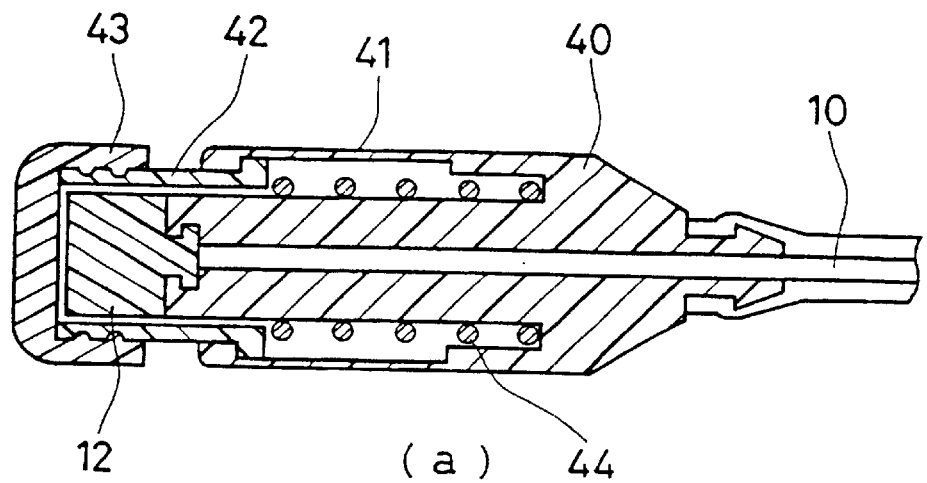
FIG. 16 is a cross sectional view of a tube connector to which a protective cover is attached.
Figure 16:
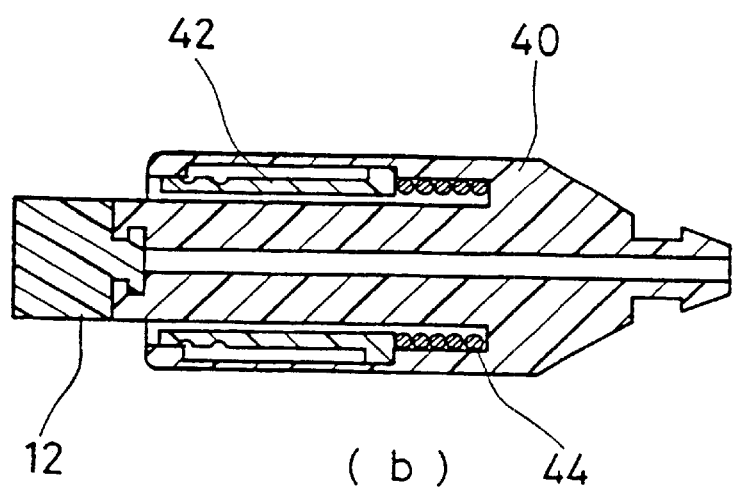

The protective cover can be formed so as to move in the channel direction with the configuration as shown in FIG. 16. The first connector body 40 has a guide portion 41, and a slide member 42 that can slide while being guided by the guide portion 41 is provided. A spring 44 is provided in a gap portion inside the guide portion 41 and biases the slide member 42 outward. The slide member 42 can be positioned so as to cover the protective cap 12 and to expose it. As shown in FIG. 16(a), the protective cover 43 is attached to the slide member 42 at the position that enables the protective cap 12 to be covered. In using the first connector, as shown in FIG. 16(b), the protective cover 43 is detached and the slide member 42 is retracted to expose the protective cap 12. Since the slide member 42 is biased by the spring 44 to be positioned to cover the protective cap 12, the protective cap 12 is covered easily and securely when the first connector is not used.

When three inflow/outflow ports are provided, it is preferable that the cap receiving recess 18 for receiving a used protective cap and the cap receiving recess 19 for receiving an unused protective cap are positioned in the neighborhood so that a circumferential angle formed between them is less than 120 degrees. Further, it is preferable that the cap receiving recess 18 and the cap receiving recess 19 are provided within the same area selected from the two areas divided by the channel so that the consistency with the channel switching is obtained.

Further, in the case of replacing the used protective cap by the unused protective cap, when a patient carries out the replacement by his hands, there is a possibility that the protective cap might be contaminated by the hands of the patient. In order to prevent such contamination, it also is effective to provide an unused protective cap in the device at the time of initial delivery.

As described above, according to the present embodiment, a patient can carry out the peritoneal dialysis easily and securely by himself. Moreover, the protective cap can be replaced without using hands, thus enabling the peritoneal dialysis to be operated cleanly without causing contamination.

Second Embodiment

Figure 17:
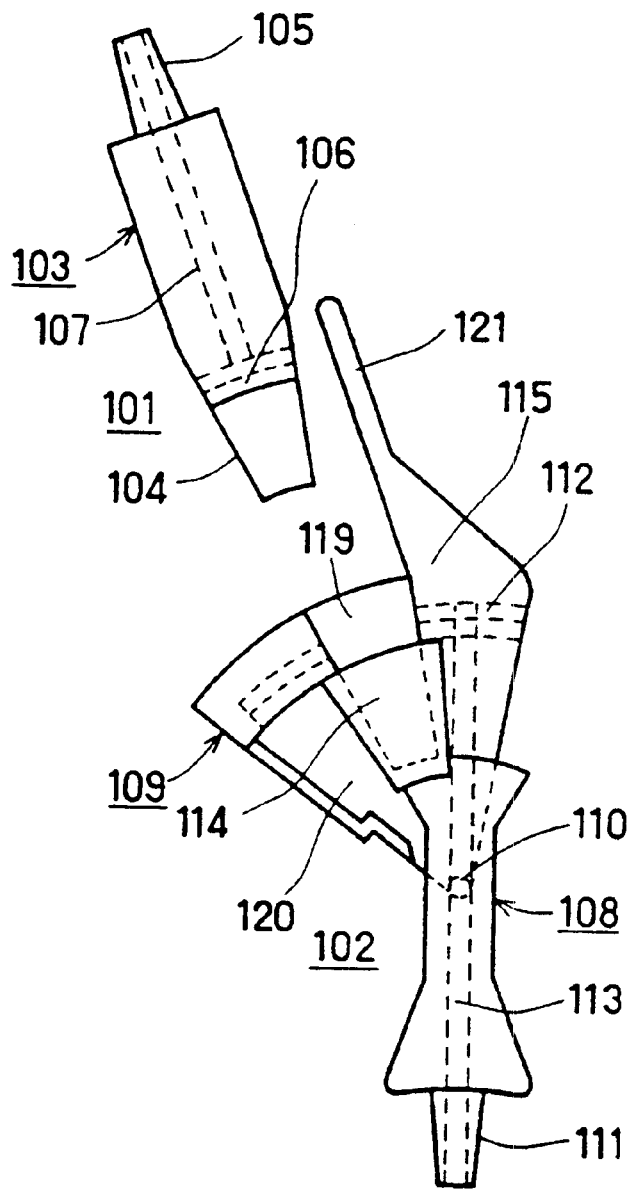
FIG. 17 is a plan view showing a medical tube-connector device according to a second embodiment of the present invention.

FIG. 17 is a plan view showing a medical tube-connector device according to a second embodiment of the present invention. Numerals 101 and 102 indicate a first connector and a second connector. Each of them is connected to a tube forming a fluid channel, which is not shown in the figure, and by coupling the connectors 101 and 102 with each other, the fluid channels communicate. The connectors 101 and 102 can be connected to and disconnected from each other.

The first connector 101 is formed of a first connector body 103 and a first cap 104. The first cap 104 can be attached to or detached from the first connector body 103. In the first connector body 103, a connection part 105 is formed for being connected to a tube (not shown in the figure). Inside the first connector body 103, a channel 107 is formed while extending from the connection part 105 to an end 106 on the side on which the first cap 104 is attached. The first cap 104 covers and seals the end 106 of the channel 107 when attached.

The second connector 102 is formed of a second connector body 108 and a guide cap 109 is provided so as to be capable of being displaced relatively with respect to the second connector body 108. The guide cap 109 is displaced by the pivot movement on an axis 110.

In the second connector body 108, a connection part 111 is formed to be connected with a tube (not shown in the figure). Inside the second connector body 108, a channel 113 is formed, which extends from the connection part 111 to the end 112 on the side opposite to the connection part 111. The second connector body 108 has a concave part 114 adjacent to the channel 113.

The guide cap 109 is provided with a cover portion 115. The cover portion 115 covers the end portion of the second connector body 108 in the state shown in FIG. 17, i.e. in the state where the second connector body 108 is pivotally moved to the end in the clockwise direction (hereinafter referred to as a "pivot right end"). In this state, the cover portion 115 covers and seals the end 112 of the second connector body 108. A handle 121 extends from the cover portion 115. Further, in the guide cap 109, an opening 119 is formed adjacent to the cover portion 115. In the state where the concave part 114 of the second connector body 108 is in the position opposing the opening 119 as shown in FIG. 17, the concave part 114 is open to the outside and the first cap 104 of the first connector 101 can be inserted. Furthermore, a receiving part 120 for receiving the first cap is formed adjacent to the opening 119.

Figure 18:
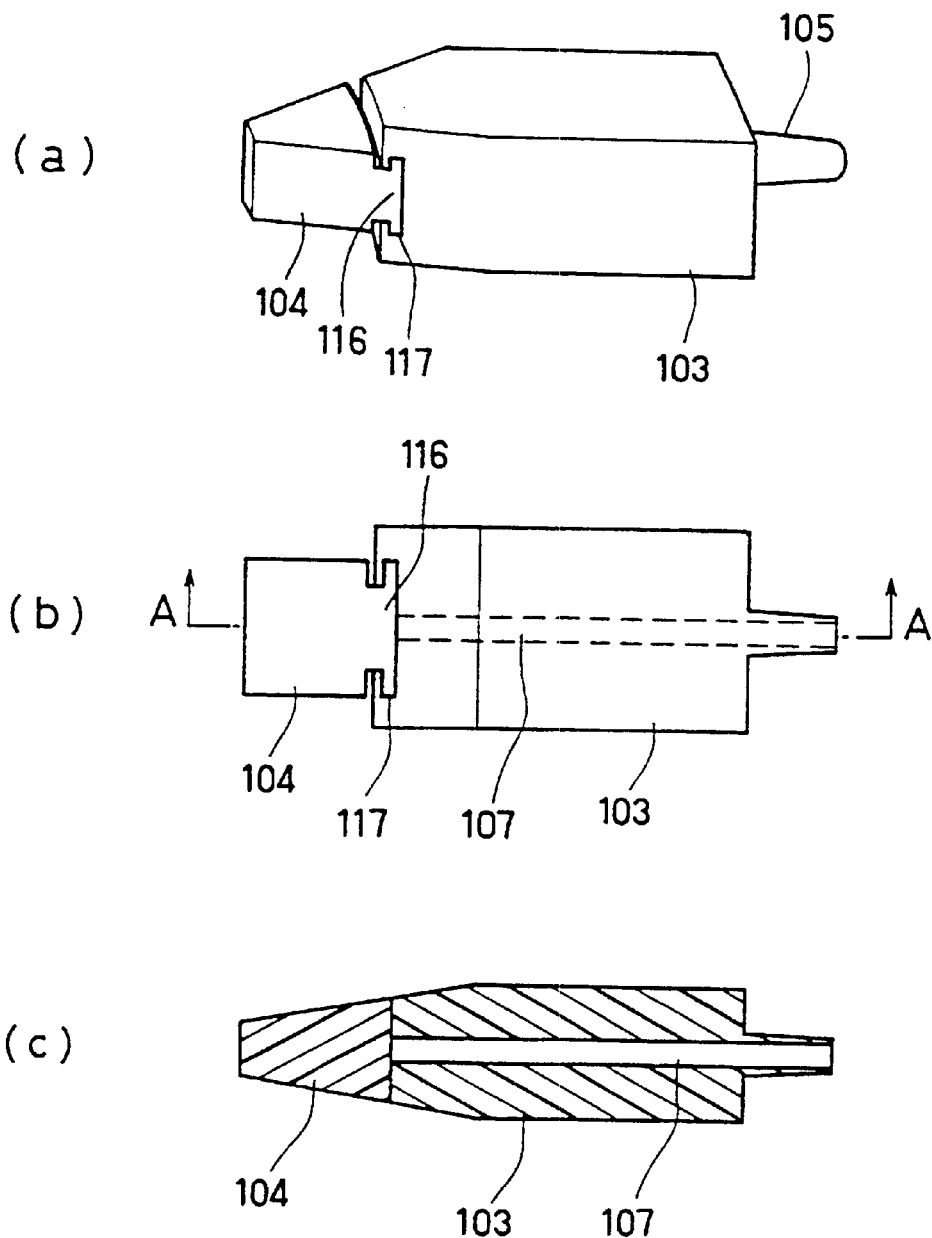
FIG. 18 shows a first connector in the device shown in FIG. 17.

Next, the configuration of the first connector 101 is described further in detail with reference to FIG. 18. FIG. 18(*a*) is a perspective view of the first connector 101, FIG. 18(*b*) is a front view of the same, and FIG. 18(*c*) is a cross sectional view taken along line A-A in FIG. 18(*b*). The first cap 104 has a convex engagement part 116 with a T-shaped cross section. The first connector body 103 has a concave engagement part 117 with a T-shaped cross section into which the convex engagement part 116 is fitted. By sliding the convex engagement part 116 with respect to the concave engagement part 117, the first cap 104 is attached to or detached from the first connector body 103.

Figure 19:
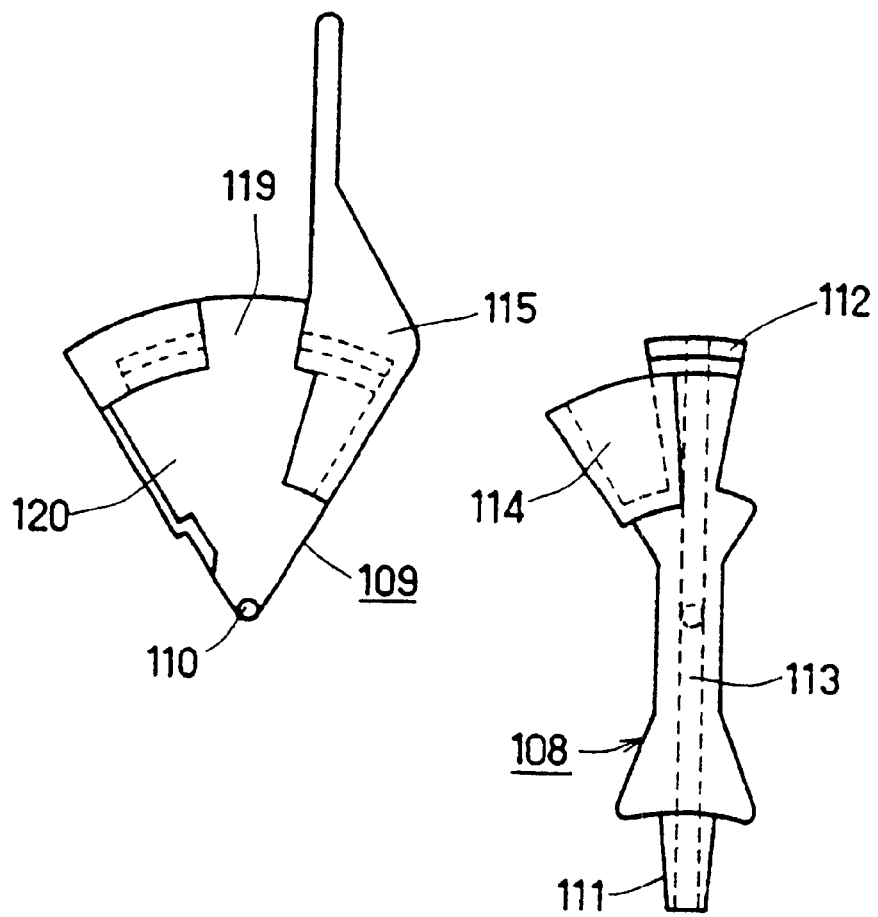
FIG. 19 is an exploded plan view of a second connector body and a guide cap in the device shown in FIG. 17.
Figure 20:
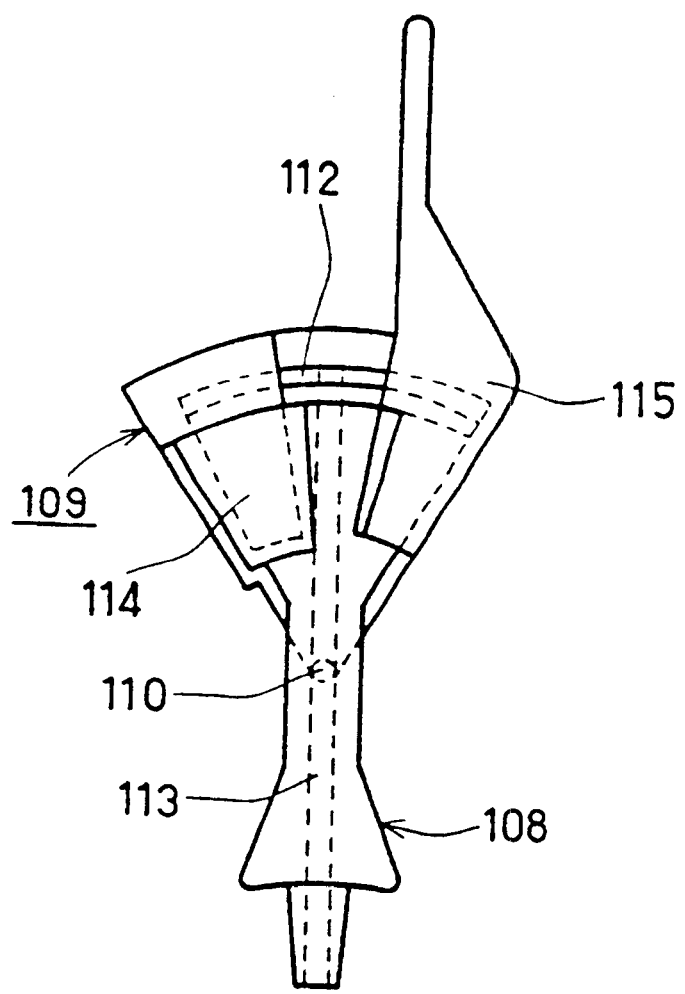
FIG. 20 is a plan view showing the state in which the second connector body in the device shown in FIG. 17 is positioned at the pivot left end.

With reference to FIGS. 19 to 22, the configuration of the second connector 102 is described further in detail as follows. FIG. 19 shows an exploded view of the second connector body 108 and the guide cap 109. Although FIG. 19 does not show the first connector, the second connector body 108 and the guide cap 109 can be detached vertically in the connected state in which respective channels of the first connector and the second connector are linked to each other. FIG. 20 shows the state where the second connector body 108 is pivotally moved to the end in the counterclockwise direction (hereinafter referred to as a "pivot left end"). In a practical use, such a state does not occur, but it is shown for the understanding of the configuration. In this state, the end 112 is exposed and the channel 113 is open at its end.

Figure 21:
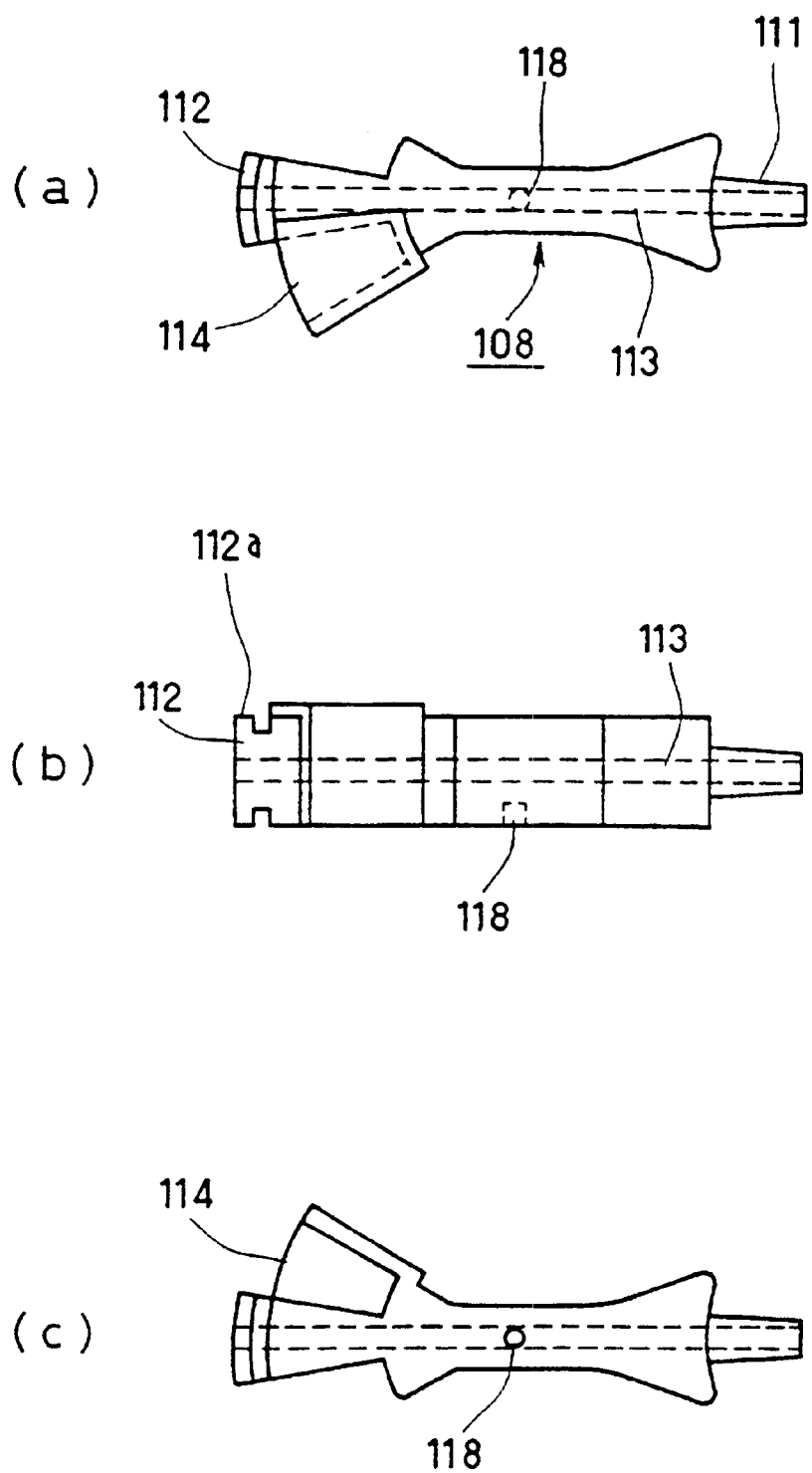
FIG. 21 shows the second connector body in the device shown in FIG. 17.

FIG. 21(*a*) is a plan view of the second connector body 108, FIG. 21(*b*) is its front view, and FIG. 21(*c*) is its rear view. In the second connector body 108, a center hole 118 for the pivot movement is formed. When the second connector body 108 and the guide cap 109 are engaged with each other, the center hole 118 and the axis 110 are fitted.

The end 112 of the second connector body 108 has a convex engagement part 112*a* with the same T-shaped cross section as that of the convex engagement part 116 in the first cap 104 as shown in FIG. 21(*b*). Therefore, this convex engagement part 112*a* enables the end 112 to fit into the concave engagement part 117 of the first connector body 3. The concave part 114 is sized to receive the first cap 104 but not the first connector body 103 when the first connector 101 is inserted.

Figure 22:
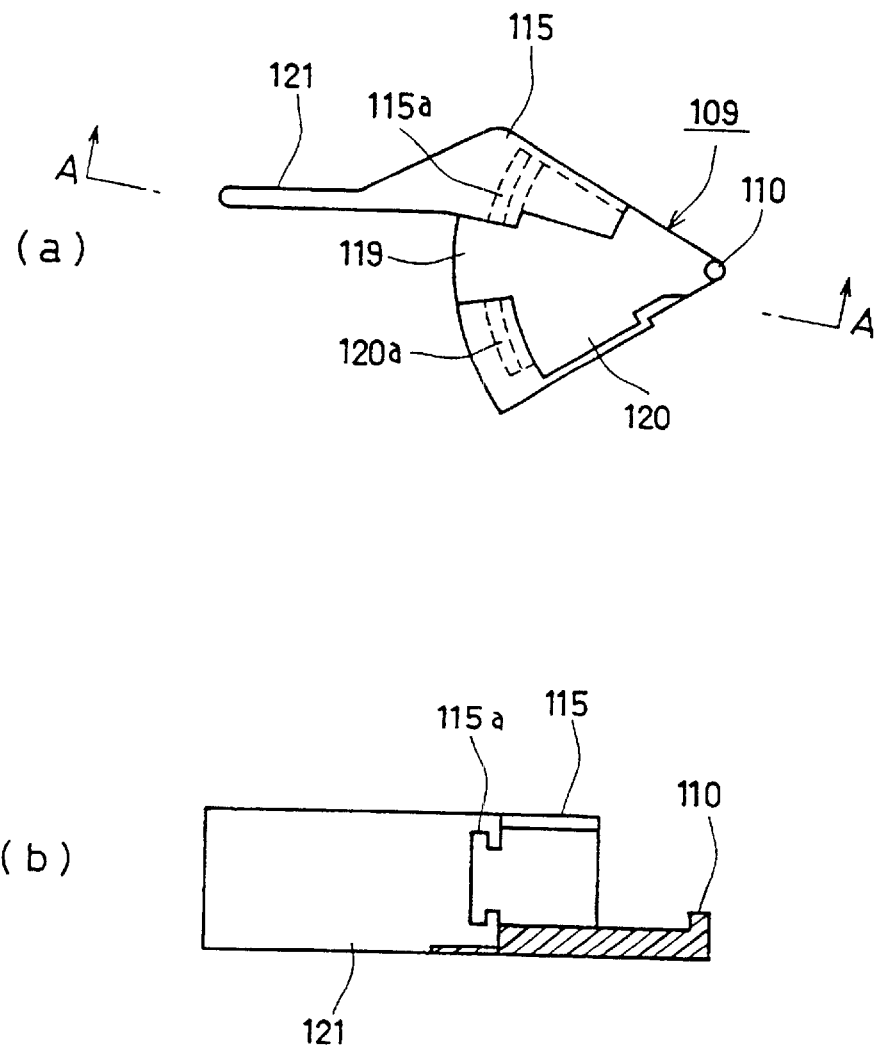
FIG. 22 shows a guide cap in the device shown in FIG. 17.

FIGS. 22(*a*) and 22(*b*) are a plan view and a front view of the guide cap 109, respectively. As shown in FIG. 17, the end 112 of the second connector body 108 is housed in the cover portion 115 of the guide cap 109 by the pivot movement. An engagement part 115*a* is formed in the cover portion 115. This concave engagement part 115*a* has the same shape as that of the concave engagement part 117 in the first connector body 103. Therefore, in the state shown in FIG. 17, the convex engagement part 112*a* of the second connector body 108 (see FIG. 21(*b*)) fits into the concave engagement part 115*a*. A receiving part 120 has an engagement part 120*a* with the same cross sectional shape as that of the concave engagement part 115*a* and can house the first cap by the pivot movement.

In the state shown in FIG. 17, the end 112 of the second connector body 108 is sealed by the cover portion 115 at the pivot right end through the relative pivot movement of the second connector body 108 and the guide cap 109. This state is a preparatory state before the channels are connected. The state as shown in FIG. 20 in which the end 112 opposes the opening 119 at the pivot left end and the end of the channel 113 is exposed is a connected state in which the channels are connected. FIG. 20 shows only the second connector 102, but the first connector body 103 is connected to the end 112 in actual use as described later.

Figure 23:
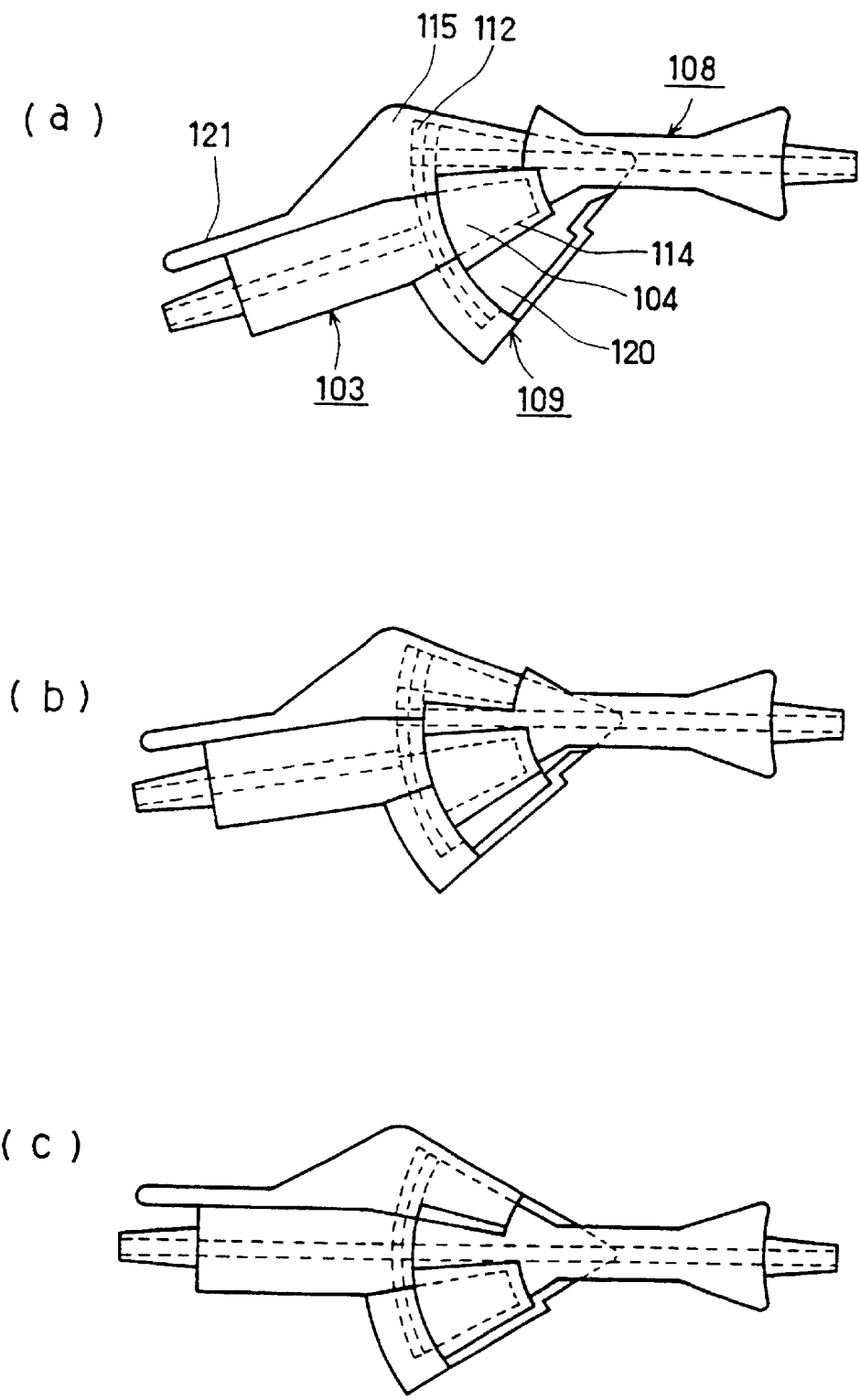
FIG. 23 shows various states during the operation of the device shown in FIG. 17.
Figure 24:
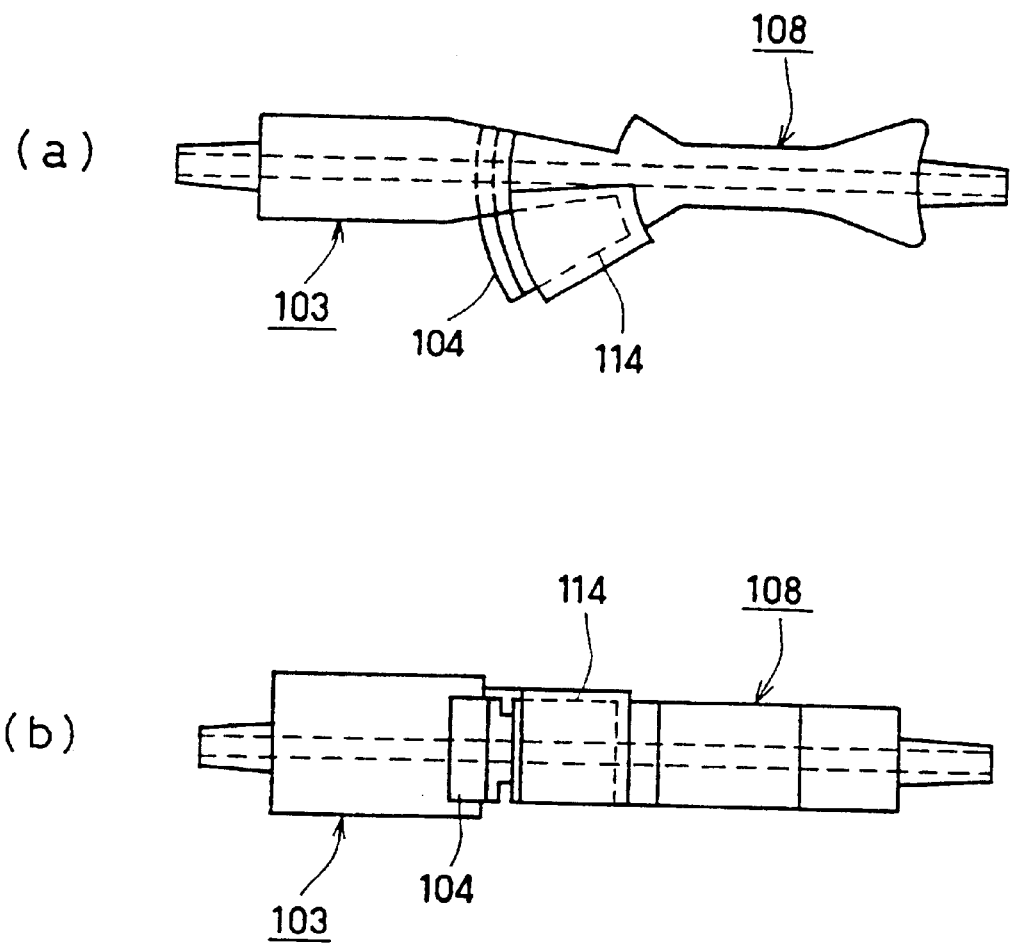

The operation in connecting and disconnecting the first connector 101 and the second connector 102 is described with reference to FIG. 23 and FIG. 24. In the state shown in FIG. 23(*a*), the second connector 102 is in the preparatory state and the first cap 104 is inserted into the concave part 114 of the second connector body 108. FIG. 23(*b*) shows the state in which the second connector body 108 is pivotally moved slightly counterclockwise. With the pivot movement, the first cap 104 is pushed by the side wall of the end 112 of the second connector body 108 and slides on the concave engagement part 117 of the first connector body 103, thus moving toward the receiving part 120. At the same time, the convex engagement part 112*a* of the second connector body 108 slides and starts fitting to the concave engagement part 117 of the first connector body 103. In other words, the first cap 104 is replaced by the end 112 of the second connector body 108 with respect to the coupling to the concave engagement part 117.

FIG. 23(*c*) shows the state in which the second connector body 108 is moved pivotally to the pivot left end. In this state, the first cap 104 has been replaced by the end 112 completely. In other words, the first cap 104 is housed in the receiving part 120 and the end 112 opposes the first connector body 103. Thus, the channel 107 of the first connector body 103 and the channel 113 of the second connector body 108 are connected to communicate with each other. The first connector body 103 and the end 112 are coupled in the same state as that in which the first connector body 103 and the first cap 104 are coupled and therefore are not separated.

In this state, as described above, the second connector body 108 can be detached from the guide cap 109. FIG. 24 shows the state in which the guide cap 109 has been detached. In this state, the guide cap 109 maintains the first cap 104 in the receiving part 120. In an ordinary use, a new guide cap 109 in which a new first cap 104 has been stored is prepared and is newly attached to the second connector body 108, and is moved pivotally. After that, the operation for disconnecting the first connector and the second connector is carried out, which is described in the following.

Next, the operation for disconnecting the first connector and the second connector from each other is described. By the pivot movement from the state shown in FIG. 23(c) to the state shown in FIG. 23(a), the first cap 104 is attached to the first connector body 103 and the end 112 of the second connector body 108 is housed in the cover portion 115, thus sealing the channel 113. In the above-mentioned operation, even when the first cap 104 is detached from or attached to the first connector body 103, the channel of the connector is protected and thus can be prevented from being contaminated.

In carrying out the above-mentioned operation, when the second connector body 108 is moved pivotally by the first connector body 103 and the handle 121 that are held together, the connection or disconnection between the first connector body 103 and the second connector body 108 can be operated stably.

In a single bag system in which a dialysate bag and a drainage bag are separately detached or attached, the peritoneal dialysis accompanied with the operation for connector detachment or attachment and the operation for fluid infusion or discharge using the medical tube connector device with the above-mentioned configuration is carried out as follows.

Figure 25:
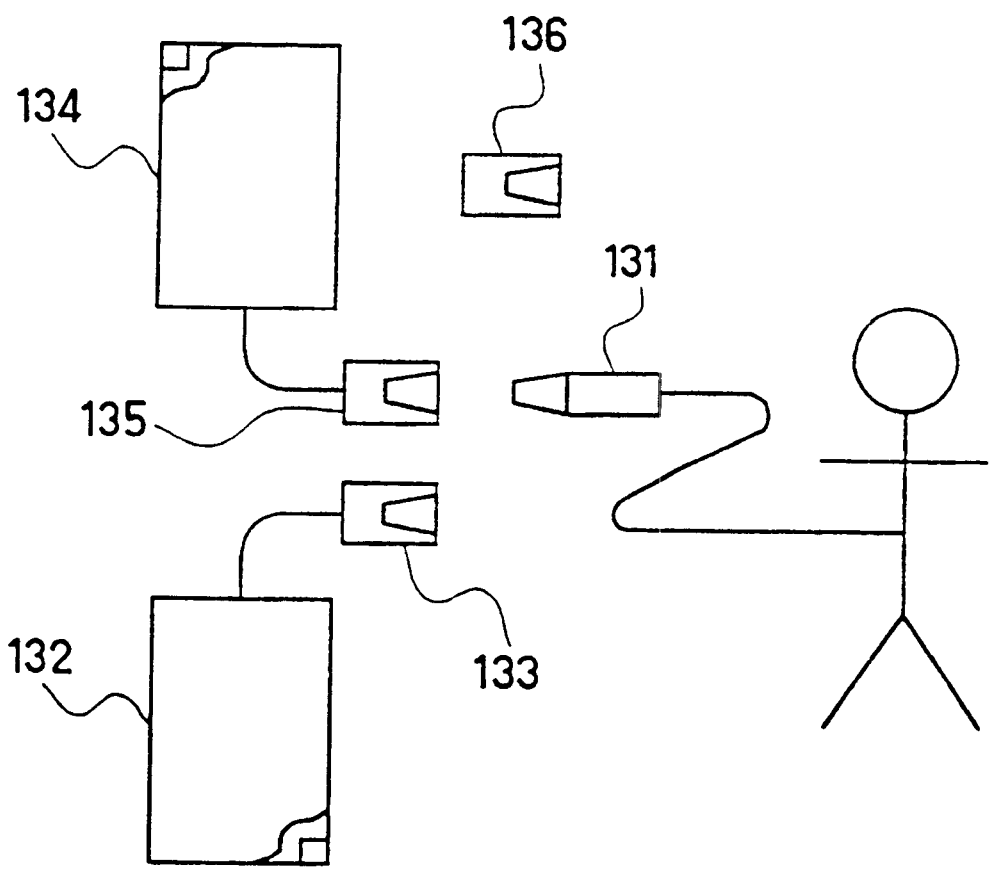
FIG. 25 is a schematic view showing the manner of connecting a connector device of the present invention in a single bag system.

(1) Connection with Drainage Bag: As shown in FIG. 25, a tube connector 131 on the patient side is formed of the first connector (with the first cap). A tube connector 133 on the drainage bag side is formed of the second connector (with the guide cap) connected to a drainage bag 132 through a tube. The patient and the drainage bag 132 are connected by connecting the tube connector 131 and the tube connector 133.

(2) Drainage: The connector device is changed from the "preparatory state" to the "connected state" to link the channels on the drainage bag side and the patient side and then the pooled liquid is discharged to the drainage bag 132 from the body of the patient.

(3) Detachment from Drainage Bag: The connector device is changed from the "connected state" to the "preparatory state" to bring the channel into a closed state. The tube connector 131 and the tube connector 133 are detached and the drainage bag 132 containing the pooled liquid that has been discharged is disposed of The patient is liberated from the drainage bag 132. The first cap is attached to the tube connector 131, and therefore the tube connector 131 is prevented from being contaminated.

(4) Connection with Dialysate Bag: The tube connector 131 is connected to a tube connector 135 on the dialysate bag side (having the configuration of the second connector) that is connected to a dialysate bag 134 through a tube. A receiving part 120 for receiving the first cap may be provided in the tube connector 135 connected to the dialysate bag. However, even when the receiving part 120 is not provided, there is no particular problem.

(5) Dialysate Infusion: The connector device is changed from the "preparatory state" to the "connected state" to link the channels on the dialysate bag side and the patient side and then new dialysate is infused into the body of the patient.

(6) Cap Replacement: While maintaining the "connected state" in which the channels on the dialysate bag side and the patient side are linked, the guide cap is detached from the tube connector 135 formed of the second connector. In this case, the first cap of the tube connector 131 remains in the guide cap. That is to say, in the tube connector 131 and the tube connector 135, the guide cap retaining the first cap is detached with the first connector body and the second connector body being connected to each other. (In this case, a guide cap for replacement is required to have the receiving part 120 for receiving the first cap.) Then, a new guide cap 136 (that has been provided with the new first cap) packed together with the dialysate bag is attached to the above-mentioned connectors (the first and the second connectors) whose bodies are connected to each other. Thus, the tube connector 135 is replaced by the new first and guide caps.

(7) Separation from Dialysate Bag: In the tube connector 135, the second connector body is displaced with respect to the guide cap to change the "connected state" into the "preparatory state", thus closing the channel. After that, the tube connector 135 and the tube connector 131 are detached. At this time, the new first cap has been attached to the tube connector 131. By the operation described above, the patient is liberated from the dialysate bag 134. The dialysate bag 134 to which the detached tube connector 135 has been connected can be used as a drainage bag at the next time. Therefore, it is desirable to reserve it until the next discharge.

As briefly explained in the above description about the operations, there is no particular problem even when the guide cap of the tube connector 135 initially connected to the dialysate bag 134 is not provided with the receiving part 120. However, it is desirable to provide the receiving part 120 (for receiving the first cap) in the new guide cap to replace the old one in (6).

Figure 26:
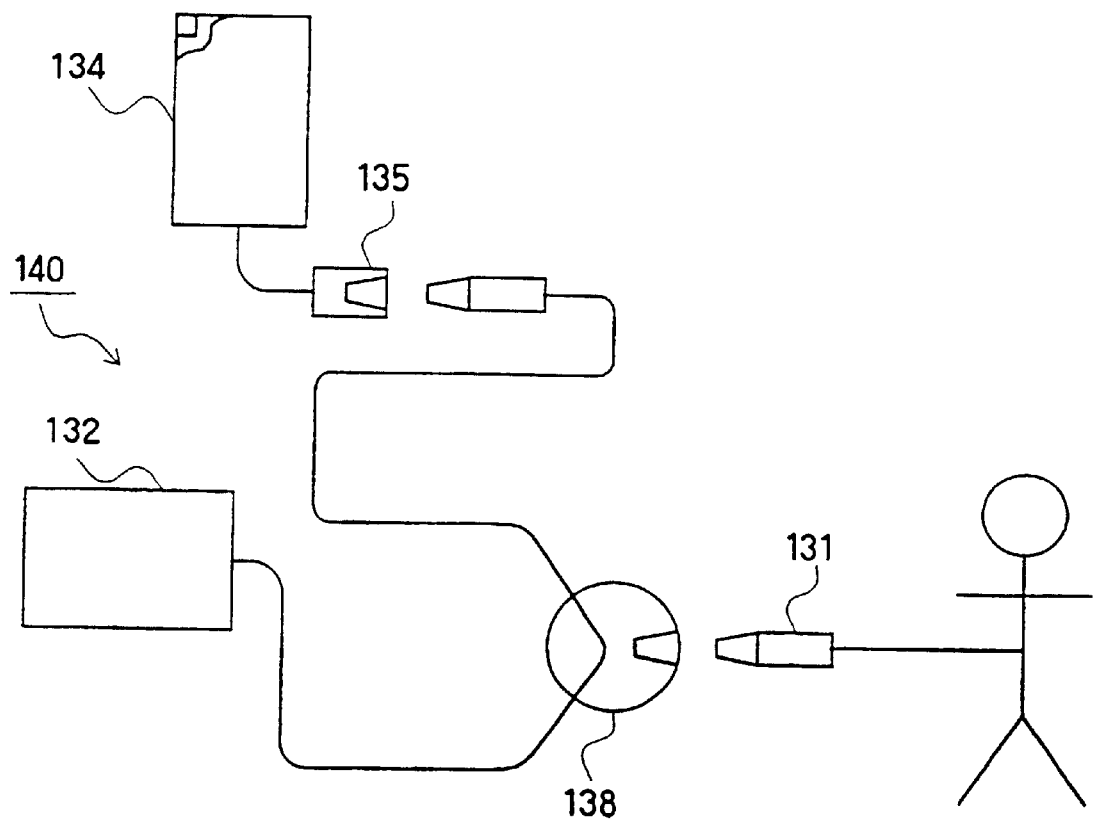
FIG. 26 is a schematic view showing an application example of a connector device of the present invention to a bag free system.
Figure 27:
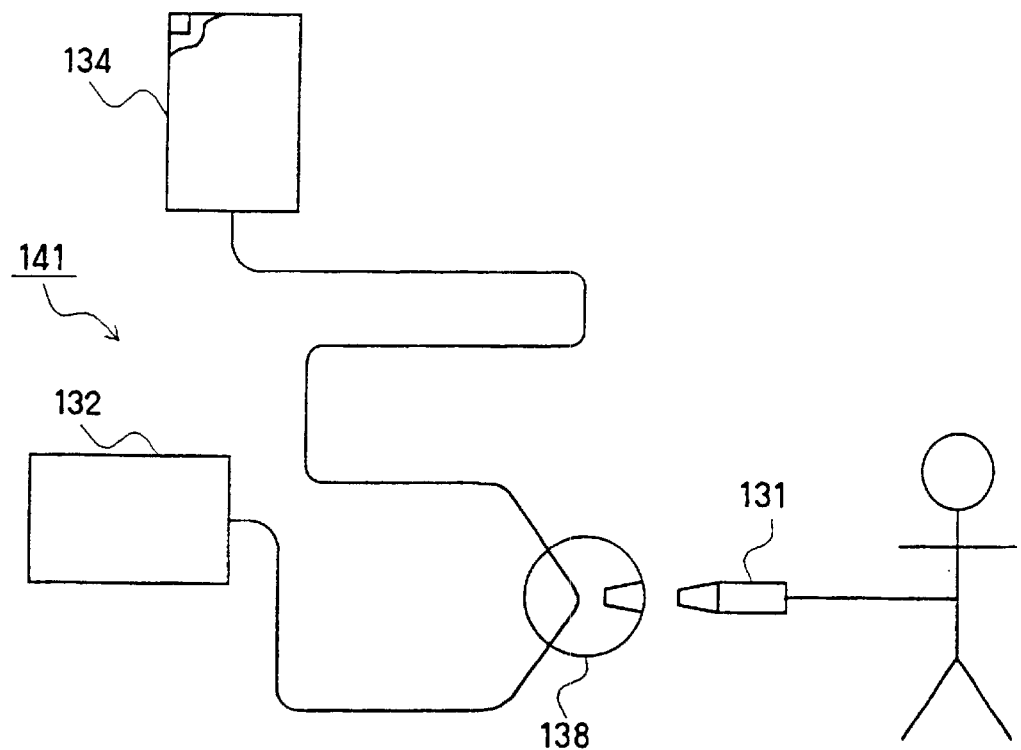
FIG. 27 is a schematic view showing an example in which a connector device of the present invention is allowed to cooperate with a twin bag system.
Figure 28:
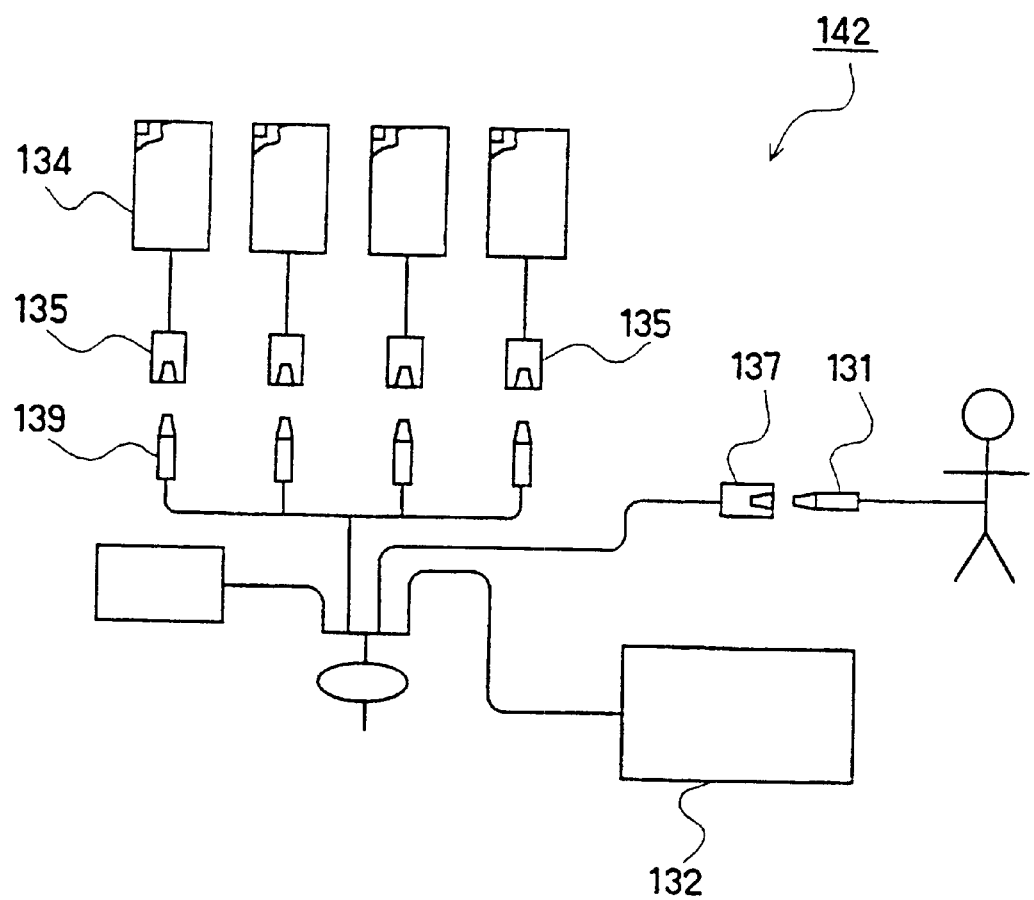
FIG. 28 is a schematic view showing the manner of connecting connector devices of the present invention in an APD apparatus.

The above description is directed to the single bag system, but as shown in FIG. 26, the device of the present invention also can be applied to a bag free system 140 in which a drainage bag, a connection part with a patient, and a connection part with a dialysate bag are connected by a branch pipe. Further, as shown in FIG. 27, the device of the present invention also can be adapted to the application form obtained by being combined with a twin bag system 141. In addition, as shown in FIG. 28, the device of the present invention also can be applied to an APD (automatic peritoneal dialysis) system 142 in which liquid infusion/discharge, preparation, and the like are automated. In FIGS. 26–28, the same members as in FIG. 25 are indicated with the same numbers and the descriptions thereof are not repeated.

In the case where liquid is infused or discharged with two bags being linked as in the bag free system 140 shown in FIG. 26, the twin bag system 141 shown in FIG. 27, or the like, the device can be operated more easily when the connection and disconnection with the first connector 131 are carried out using a second connector 138 with the configuration shown in the first embodiment.

The connectors used when a dialysate is prepared from a plurality of dialysate bags in the APD system 142 shown in FIG. 28, i.e. the tube connectors 135 on the dialysate side that are connected to the tube connectors 139 (the first connectors) shown in FIG. 28, are not required to be restored to the "preparatory state" again after being changed from the "preparatory state" to the "connected state". The tube connectors 135 can be simplified so as to be disposed while remaining in the "connected state". However, even in this case, since it is necessary to attach a cap to the connector on the patient side, the tube connector 137 connected to the tube connector 131 on the patient side is required to have a mechanism for changing its state as follows: "the preparatory state" →"the connected state" "the preparatory state".

INDUSTRIAL APPLICABILITY

According to the medical tube-connector device of the present invention, the connection and disconnection between connectors are carried out without exposing the ends of the channels provided in the connectors. Therefore, the ends can be prevented from being contaminated by floating bacteria in the outside air. In addition, the connection parts are not touched directly by hands of a patient in connecting and disconnecting the connectors. Thus, the channel ends are not contaminated or damaged by hands. Moreover, the connection and disconnection between connectors can be operated without using any special tool and therefore the operation is very easy.

What is claimed is:

1. A medical tube-connector device having two connectors for connecting tubes, the two connectors being connectable to or disconnectable from each other, comprising:
   a first connector, including:
      a first connector body having a channel extending through its inside and being connectable to a tube at one end of the channel; and
      a protective cap capable of being attached to or detached from the first connector body for covering and sealing the other end of the channel in a state in which the protective cap has been attached to the first connector body; and
   a second connector, including:
      a second connector body having a channel extending through its inside and a concave part into which the protective cap of the first connector can be inserted, the second connector body being connectable to a tube at one end of the channel; and
      a guide cap capable of being displaced with respect to the second connector body and being provided with a cover portion for covering and sealing the other end of the channel in the second connector body,
   wherein the second connector body and the guide cap can be brought into a preparatory state or a connected state by their relative displacement, in the preparatory state the concave part of the second connector body being open and the other end of the channel being sealed by the cover portion, and in the connected state the other end of the channel being open, and
   by inserting the first connector with the protective cap attached into the concave part in the preparatory state and then bringing the second connector body and the guide cap into the connected state, the protective cap is moved while being retained in the concave part so as to be detached from the first connector body and at the same time the first connector body and the second connector body are connected, thus allowing their channels to communicate.

2. The medical tube-connector device according to claim 1, wherein the second connector comprises:
   a casing having an annular shape and functioning as the guide cap, the casing having, at its periphery:
      at least one inflow/outflow port for liquids, which can be connected to a tube; and
      an insertion opening into which the first connector can be inserted;
   a rotor being formed of a substantially cylindrical body mounted rotatably inside the casing and functioning as the second connector body, the rotor having:
      a fluid channel extending through an inside of the cylindrical body and forming inflow/outflow ports on a peripheral surface of the cylindrical body; and
      at least one cap receiving recess being formed on the peripheral surface of the cylindrical body and being capable of receiving a protective cap attached to the first connector,
   wherein the rotor and the casing can be brought into a preparatory state or a connected state depending on their relative rotational positions, in the preparatory state the insertion opening of the casing opposing the cap receiving recess in the rotor and the inflow/outflow ports of the rotor being sealed by the casing, and in the connected state the insertion opening of the casing opposing one of the inflow/outflow ports of the rotor and an inflow/outflow port of the casing and the other inflow/outflow port of the rotor communicating with each other, and
   by inserting the first connector in the preparatory state into the cap receiving recess through the insertion opening from a side of the protective cap and then bringing the rotor and the casing into the connected state, the protective cap is moved while being retained in the cap receiving recess of the rotor so as to be detached from the first connector body and at the same time the channels of the first connector body and of the rotor communicate.

3. The medical tube-connector device according to claim 2, wherein in the connected state, the first connector body is maintained by being fitted at a periphery of the rotor.

4. The medical tube-connector device according to claim 3, wherein the protective cap can be detached from or attached to the first connector body by its sliding movement in a direction substantially orthogonal to a direction of the channel.

5. The medical tube-connector device according to claim 3, wherein the protective cap is attached to the first connector body through the fitting between a convex part with a T-shaped cross section provided in the protective cap and a concave part with a T-shaped cross section provided in the first connector body, and a convex part with the same T-shaped cross section as in the protective cap is provided at the periphery of the rotor except for the insertion opening.

6. The medical tube-connector device according to claim 1, wherein the protective cap is attached to the first connector body and at the same time a channel end of the second connector body is sealed by the cover portion by relatively displacing the second connector body and the guide cap from the connected state and thus restoring them into the preparatory state.

7. The medical tube-connector device according to claim 1, wherein in the connected state, the guide cap can be detached from the second connector body in a state where the first connector body and the second connector body are maintained in a coupled state.

8. The medical tube-connector device according to claim 7, wherein a receiving part capable of receiving the protective cap is formed in the guide cap adjacent to a place where the first connector is inserted, and in the connected state, the protective cap having been moved while having been maintained in the concave part is received and maintained in the receiving part.

9. The medical tube-connector device according to claim 7, wherein the first connector and the second connector can maintain the connected state against a pulling force in a direction of the channel and can be disconnected by their sliding movements with respect to each other in a direction orthogonal to the direction of the channel.

10. The medical tube-connector device according to claim 1, wherein the protective cap can be attached to or detached from the first connector body by its sliding movement along a circular arc, the second connector body and the guide cap can be displaced relatively by their sliding movements along a circular arc, the circular arc corresponding to a sliding face for the sliding movement between the first connector body and the protective cap has the same radius as that of the circular arc corresponding to a sliding face for the sliding movements between the second connector body and the guide cap, and the sliding face between the first connector body and the protective cap and the sliding face between the second connector body and the guide cap are arranged on the same circular arc when the first connector is inserted into the concave part from a side of the protective cap in the preparatory state.

11. The medical tube-connector device according to claim 10, wherein a center of the circular arc corresponding to the sliding face between the second connector body and the guide cap is positioned inside the second connector body.

12. The medical tube-connector device according to claim 10, wherein the first connector body has any one of a concave engagement part and a convex engagement part, each of which has a T-shaped cross section orthogonal to a direction of its sliding movement, the protective cap has the other one of the concave engagement part and the convex engagement part, the concave engagement part and the convex engagement part are fitted to each other to lead sliding movements of the first connector body and the protective cap, and by the fitting, the protective cap is maintained in the first connector body.

13. The medical tube-connector device according to claim 12, wherein when the first connector body has the concave engagement part with the T-shaped cross section, the second connector body has the convex engagement part with the T-shaped cross section, and when the first connector body has the convex engagement, the second connector body has the concave engagement part with the T-shaped cross section, in the preparatory state, when the protective cap is inserted into the concave engagement part, the convex and concave engagement parts of the protective cap and the second connector body are arranged on the same circular arc, and in the connected state, the convex and concave engagement parts of the first connector body and the second connector body are fitted, thus coupling the first connector body and the second connector body.

14. The medical tube-connector device according to claim 1, wherein the guide cap has a wall for covering the protective cap in the connected state.

15. The medical tube-connector device according to claim 1, wherein the guide cap has a handle extending along the inserted first connector body.

16. A cap for replacement formed by a combination of the guide cap and the protective cap in the medical tube-connector device according to claim 1, comprising:

the guide cap provided with a cover portion that can cover and seal the other end of the channel of the second connector body, an opening adjacent to the cover portion, and a receiving part that is adjacent to the opening and that can receive the protective cap; and the protective cap received in the receiving part of the guide cap.

17. A connector that is one of two connectors being connectable to or disconnectable from each other for connecting tubes so as to form a medical tube-connector device, comprising:

a casing with an annular shape, having, at its periphery:
at least one inflow/outflow port for liquids, which can be connected to a tube; and
an insertion opening into which the other connector can be inserted together with a protective cap for sealing an opening of the other connector;

a rotor being formed of a substantially cylindrical body mounted rotatably inside the casing, the rotor having:
a fluid channel extending through an inside of the cylindrical body and forming inflow/outflow ports on a peripheral surface of the cylindrical body; and
at least one cap receiving recess being formed on the peripheral surface of the cylindrical body and being capable of receiving the protective cap for sealing the opening of the other connector, wherein the rotor and the casing can be brought into a preparatory state or a connected state depending on their relative rotational positions, in the preparatory state the insertion opening of the casing opposing the cap receiving recess in the rotor and thus the inflow/outflow ports in the rotor being sealed by the casing, and in the connected state the insertion opening of the casing opposing one of the inflow/outflow ports of the rotor and the inflow/outflow port of the casing and the other inflow/outflow port of the rotor communicating with each other, and by inserting the other connector in the preparatory state into the cap receiving recess through the insertion opening and then bringing the rotor and the casing into the connected state, the protective cap for sealing the other connector is retained in the cap receiving recess so as to be detached from the connector and at the same time the channels of the other connector and the rotor communicate.

18. The connector according to claim 17, wherein the rotor comprises at least two cap receiving recesses and the insertion opening of the casing can oppose any of the cap receiving recesses by the relative rotational movement between the rotor and the casing.

19. The connector according to claim 18, wherein unused protective caps are supplied to the cap receiving recesses while at least one cap receiving recess is kept empty, and the rotor is rotated from a state in which the rotor is connected with the other connector, to have a positional relationship in which the insertion opening of the casing opposes any one of the cap receiving recesses in which the unused protective caps have been supplied, thus attaching an unused protective cap to the other connector.

20. The connector according to claim 17, wherein the casing has at least two inflow/outflow ports for liquids, one of the inflow/outflow ports communicates selectively with one of the inflow/outflow ports of the rotor by a rotational movement of the rotor, and at the same time, the other inflow/outflow port of the rotor opposes the insertion opening of the casing.

21. The connector according to claim 20, wherein the casing has two inflow/outflow ports for liquids, and the two of the inflow/outflow port and the insertion opening are spaced substantially at 120 degrees at the periphery of the casing.

22. A connector that is one of two connectors being connectable to or disconnectable from each other for connecting tubes so as to form a medical tube-connector device, the connector comprising:

a connector body, which is attached to an end of a tube and has a through hole that communicates with the tube; and a protective cap, which is attached to the connector body and seals an opening of the connector body, wherein the protective cap is detached from or attached to the connector body by being slid in a direction substantially orthogonal to an axial direction of the through hole.

23. The connector according to claim 22, wherein the protective cap has a convex part with a T-shaped cross section, the connector body has a concave part with a T-shaped cross section, and the protective cap and the connector body are coupled by fitting between the convex part and the concave part.

24. A connector that is one of two connectors being connectable to or disconnectable from each other for connecting tubes so as to form a medical tube-connector device, comprising:

a connector body having a channel extending through its inside and a concave part into which a protective cap for sealing an opening of the other connector can be inserted, the connector body being connectable to a tube at one of the channel; and a guide cap capable of being displaced with respect to the connector body and being provided with a cover portion for covering and sealing the other end of the channel of the connector body, wherein the connector body and the guide cap can be brought into a preparatory state or a connected state by their relative displacement, in the preparatory state the concave part of the connector body being open and the other end of the channel being sealed by the cover portion and in the connected state the other end of the channel being open, and in the connected state, the guide cap can be detached from the connector body in a state where the other connector and the connector body are maintained in a coupled state.

25. The connector according to claim 24, wherein the guide cap has a receiving part capable of receiving the protective cap adjacent to a place where the other connector is inserted, and in the connected state, the protective cap having been moved while having been maintained in the concave part is received in the receiving part, and the protective cap can be maintained in the guide cap detached from the connector body.

* * * * *